United States Patent [19]

Hidaka et al.

[11] Patent Number: 4,798,897

[45] Date of Patent: Jan. 17, 1989

[54] ISOQUINOLINE DERIVATIVES

[75] Inventors: Hiroyoshi Hidaka, Tshu; Anri Morikawa, Narashino, both of Japan

[73] Assignee: Asahi Kasei Kogyo Kabushiki Kaisha, Osaka, Japan

[21] Appl. No.: 40,828

[22] Filed: Apr. 21, 1987

[51] Int. Cl.$^4$ .................. C07D 401/12; C07D 217/00
[52] U.S. Cl. ...................................... 546/139; 540/454; 540/485; 540/544; 540/597; 544/128; 546/141
[58] Field of Search ................. 546/139, 141; 544/128; 540/454, 485, 544, 597

[56] References Cited

U.S. PATENT DOCUMENTS

| | | | |
|---|---|---|---|
| 4,456,757 | 6/1984 | Hidaka et al. | 546/139 |
| 4,525,589 | 6/1985 | Hidaka et al. | 546/139 |
| 4,634,770 | 1/1987 | Hidaka et al. | |
| 4,678,783 | 7/1987 | Hidaka et al. | 546/139 |

FOREIGN PATENT DOCUMENTS 61-152658 7/1986 Japan .
61-227581 10/1986 Japan .

Primary Examiner—Richard L. Raymond
Assistant Examiner—James H. Turnipseed
Attorney, Agent, or Firm—Finnegan, Henderson, Farabow, Garrett & Dunner

[57] ABSTRACT

An isoquinoline derivative represented by the formula (I)

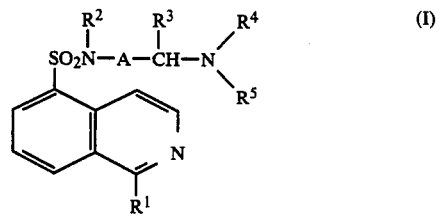

wherein $R^1$, $R^2$, $R^3$, $R^4$, $R^5$ and A are as defined in the disclosure, or a pharmacologically acceptable acid salt thereof. These compounds have an excellent relaxation action on blood vessels, particularly coronary arteries, and on bronchial tubes. Accordingly, the compounds can be advantageously utilized as drugs for prevention and treatment of angina, myocardial infarction, cardiovascular thrombosis, cerebrovascular thrombosis, hypertonia, asthma and other various circulatory and respiratory organ diseases.

13 Claims, No Drawings

ISOQUINOLINE DERIVATIVES

BACKGROUND OF THE INVENTION

1. Field Of The Invention

The present invention relates to isoquinoline derivatives. More particularly, the present invention is concerned with isoquinoline derivatives which are novel compounds that affect the vascular smooth muscle of a mammal, thereby being of value as, e.g., vasodilators, cerebral circulation ameliorators, and drugs for prevention and treatment of angina, myocardial infarction, cerebrovascular thrombosis, cardiovascular thrombosis, hypertonia and other circulatory organ diseases. The isoquinoline derivatives of the present invention also affect the bronchial smooth muscle of a mammal, thereby being valuable drugs for prevention and treatment of respiratory organ diseases such as asthma.

2. Discussion Of Related Art

Known in the art are compounds useful to treat circulatory organ diseases which are represented by the following formulae (II) to (IX):

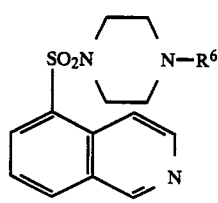

(II)

(disclosed in U.S. Pat. No. 4,525,589)

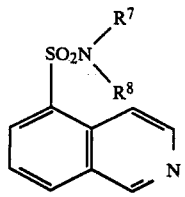

(III)

(disclosed in the above-mentioned patent)

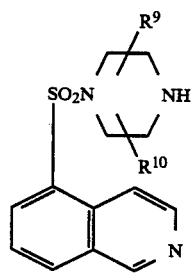

(IV)

(disclosed in the above-mentioned patent)

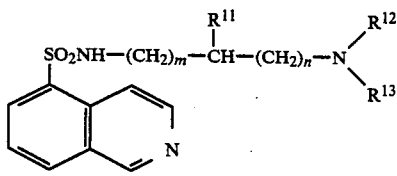

(V)

(disclosed in the above-mentioned patent)

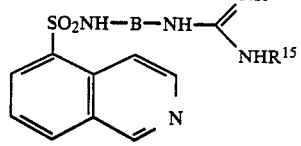

(VI)

(disclosed in U.S. Pat. No. 4,634,770)

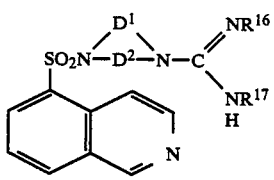

(VII)

(disclosed in the above-mentioned patent)

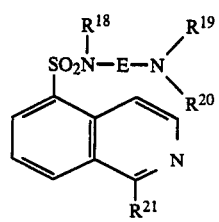

(VIII)

(disclosed in Japanese Patent Application Laid-Open Specification No. 61-152658/1986)

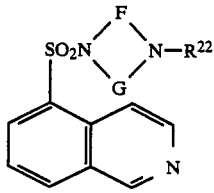

(IX)

(disclosed in Japanese Patent Application Laid-Open Specification No. 61-227581/1986)

In the above formulae, $R^6$ represents an alkyl group, an aryl group, an aralkyl group, a benzoyl group, a cinnamyl group, a furoyl group or a group of the formula:

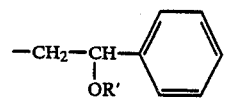

in which R' represents a lower alkyl group. $R^7$ and $R^8$ each independently represent a hydrogen atom or a lower alkyl group, or $R^7$ and $R^8$ are bonded with each other directly or through the medium of an oxygen atom or a nitrogen atom to form a heterocyclic ring in cooperation with the adjacent nitrogen atom. $R^9$ represents a hydrogen atom or an alkyl group having 1 to 10 carbon atoms. $R^{10}$ represents a group selected from alkyl, aryl and aralkyl groups each having 1 to 10 carbon atoms, and $R^{11}$ represents a hydrogen atom or a group selected from alkyl and aryl groups each having 1 to 10 carbon atoms. $R^{12}$ and $R^{13}$ each independently represent a hydrogen atom or a group selected from alkyl, aryl and aralkyl groups each having 1 to 10 carbon atoms, or $R^{12}$ and $R^{13}$ are bonded with each other directly or through the medium of an oxygen atom to form a heterocyclic ring in cooperation with the adjacent nitrogen atom. Symbols m and n each independently represent an integer of 0 to 10. B represents an alkylene group having v carbon atoms substituted with u group(s) selected from alkyl, aryl and aralkyl groups each having 1 to 10 carbon atoms, in which v is an integer not greater than 10 and u is an integer of 0 to $2 \times v$. $R^{14}$ and $R^{15}$ each independently represent a hydrogen atom or an alkyl group having 1 to 6 carbon atoms, or $R^{14}$ and $R^{15}$ are directly bonded with each other to form an alkylene group having 2 to 6 carbon atoms. $D^1$ represents an ethylene group substituted with x alkyl group(s) each having 1 to 6 carbon atoms, in which x is an integer of 0 to 4. $D^2$ represents an ethylene or trimethylene group each substituted with y alkyl group(s) each having 1 to 6 carbon atoms, in which y is an integer of 0 to 4. $R^{16}$ and $R^{17}$ each independently represent a hydrogen atom or an alkyl group having 1 to 6 carbon atoms, or $R^{16}$ and $R^{17}$ are directly bonded with each other to form an alkylene group having 2 to 4 carbon atoms. E represents an alkylene group having 2 to 6 carbon atoms and unsubstituted or substituted with an alkyl group having 1 to 6 carbon atoms. $R^{18}$ and $R^{19}$ each independently represent a hydrogen atom, a straight chain or branched alkyl group having 1 to 6 carbon atoms, or $R^{18}$ and $R^{19}$ are directly bonded with each other to form an ethylene or trimethylene group each unsubstituted or substituted with an alkyl group having 1 to 6 carbon atoms. $R^{20}$ represents a hydrogen atom, an alkyl group having 1 to 6 carbon atoms or an amidino group. $R^{21}$ represents a hydroxyl group or a chlorine atom. F represents an ethylene group unsubstituted or substituted with an alkyl group having 1 to 6 carbon atoms, a phenyl group or a benzyl group. G represents a trimethylene group unsubstituted or substituted with an alkyl group having 1 to 6 carbon atoms, a phenyl group or a benzyl group. $R^{22}$ represents a hydrogen atom or an alkyl group having 1 to 6 carbon atoms.

The above compounds may effectively increase the diameter of cerebral blood vessels. However, although the compounds effectively act on cerebral blood vessels, they have poor activity with regard to increasing the diameter of cardiac blood vessels. Hence, there is still a strong demand in the art for compounds which can more effectively increase the diameters of both cerebral and cardiac blood vessels.

SUMMARY OF THE INVENTION

We have made extensive and intensive studies on various compounds, especially isoquinoline derivatives, and their actions on cerebral and cardiac blood vessels. As a result, it has unexpectedly been found that novel isoquinoline derivatives are capable of increasing the diameter of cardiac blood vessels as well as the diameter of cerebral blood vessels and, hence, are useful to prevent and treat angina, myocardial infarction, cerebrovascular thrombosis, cardiovascular thrombosis, hypertonia and other circulatory organ diseases. Moreover, it has unexpectedly been found that these novel compounds also exert an excellent smooth muscle relaxation action on the bronchus and, hence, are valuable drugs for the prevention and treatment of respiratory organ diseases such as asthma.

It is, therefore, an object of the present invention to provide novel classes of isoquinoline derivatives which are capable of effectively increasing the diameters of cardiac blood vessels and cerebral blood vessels and exerting an excellent blood flow increase action on mammals. The novel compounds especially selectively act on coronary arterys as compared with the above-mentioned known compounds and, hence, can be advantageously utilized as drugs for the prevention and treatment of coronary vessel diseases such as angina and myocardial infarction. Moreover, the isoquinoline derivatives of the present invention exert an excellent smooth muscle relaxation action on bronchial tubes, which action is not exerted by the known compounds. Accordingly these isoquinoline derivatives are also valuable drugs for the prevention and treatment of respiratory organ diseases such as asthma.

The foregoing and other objects, features and advantages of the present invention will be apparent to those skilled in the art from the following detailed description and appended claims.

DETAILED DESCRIPTION OF THE INVENTION

According to the present invention, there is provided an isoquinoline derivative represented by the formula (I)

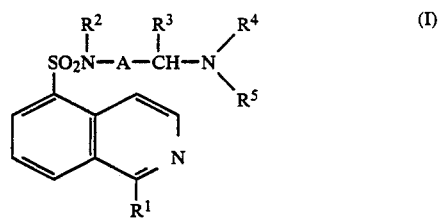

wherein
$R^1$ is selected from the group consisting of a hydrogen atom, a chlorine atom and a hydroxyl group;
$R^2$ is selected from the group consisting of an alkyl group having 1 to 8 carbon atoms and a benzyl group, or directly bonded with $R^3$ to form Z;
$R^3$ is selected from the group consisting of a hydrogen atom and an alkyl group having 1 to 8 carbon atoms, or directly bonded with $R^2$ to form Z;
said Z being selected from the group consisting of an unsubstituted ethylene group, an ethylene group substituted with an alkyl group having 1 to 8 carbon atoms, an unsubstituted trimethylene group, and a trimethylene group substituted with an alkyl group having 1 to 8 carbon atoms;
provided that
where $R^2$ and $R^3$ are not directly bonded with each other, $R^1$ is a hydrogen atom, and
where $R^2$ and $R^3$ are directly bonded with each other to form Z, $R^1$ is selected from the group consisting of a hydrogen atom, a chlorine atom and a hydroxyl group;
$R^4$ and $R^5$ are independently selected from the group consisting of a hydrogen atom, an alkyl group having 1 to 6 carbon atoms which is unsubstituted or substituted with a phenyl group, and a phenyl group, or $R^4$ and $R^5$ are each alkylene groups having 1 to 5 carbon atoms and bonded with each other directly or through an oxygen atom to form a heterocyclic ring in cooperation with the adjacent nitrogen atom, the total number of carbon atoms in the two alkylene groups not exceeding 6; and
A is an alkylene group having 1 to 5 carbon atoms which is unsubstituted or substituted with an alkyl group having 1 to 8 carbon atoms;
or a pharmacologically acceptable acid salt thereof.

In the above formula (I), where $R^2$ is an alkyl group such as a methyl, ethyl, n-propyl, isopropyl, butyl, hexyl and octyl groups or a benzyl group, and $R^3$ is a hydrogen atom or an alkyl group such as a methyl, ethyl, propyl, butyl, hexyl and octyl groups, $R^1$ is a hydrogen atom and A is a methylene, ethylene, trimethylene, tetramethylene or pentamethylene group each unsubstituted or substituted with an alkyl group having 1 to 8 carbon atoms such as a methyl, ethyl, n-propyl, isopropyl, butyl and hexyl groups.

Where $R^2$ and $R^3$ are directly bonded with each other to form an ethylene or trimethylene group each unsubstituted or substituted with an alkyl group having 1 to 8 carbon atoms such as a methyl and ethyl groups and $R^1$ is a hydrogen atom, a chlorine atom or a hydroxyl group, A is preferably an unsubstituted methylene or ethylene group or A is a methylene or ethylene group each substituted with an alkyl group having 1 to 5 carbon atoms such as a methyl and ethyl groups, and $R^2$, N, A, CH and $R^3$ cooperate together to form a heterocyclic ring, for example, a pyrrolidine ring, a piperidine ring and a perhydroazepine ring.

$R^4$ and $R^5$ may each independently represent a hydrogen atom, an alkyl group such as a methyl, ethyl, propyl, butyl, hexyl and cyclohexyl groups, a phenyl-substituted alkyl group having 1 to 6 cartbon atoms, preferably a phenyl-substituted methyl or ethyl group, or a phenyl group. Alternatively, $R^4$ and $R^5$ may each independently represent an alkylene group having 1 to 5 carbon atoms, such as an ethylene and trimethylene groups, bonded with each other directly or through an oxygen atom to form a heterocyclic ring in cooperation with the adjacent nitrogen atom. In the case where $R^4$ and $R^5$ independently represent an alkylene group bonded with each other, the total number of carbon atoms in the two alkylene groups does not exceed 6. Examples of the heterocyclic ring include a pyrrolidine ring, a piperidine ring and a morpholine ring.

Examples of the isoquinoline derivative represented by the formula (I) are as follows:

(1) N-(2-aminoethyl)-N-methyl-5-isoquinolinesulfonamide
(2) N-(2-aminoethyl)-N-isopropyl-5-isoquinolinesulfonamide
(3) N-(2-aminoethyl)-N-butyl-5-isoquinolinesulfonamide
(4) N-(2-aminoethyl)-N-hexyl-5-isoquinolinesulfonamide
(5) N-(2-aminoethyl)-N-octyl-5-isoquinolinesulfonamide
(6) N-(2-aminoethyl)-N-benzyl-5-isoquinolinesulfonamide
(7) N-(3-aminopropyl)-N-hexyl-5-isoquinolinesulfonamide
(8) N-(4-aminobutyl)-N-hexyl-5-isoquinolinesulfonamide
(9) N-(5-aminopentyl)-N-hexyl-5-isoquinolinesulfonamide
(10) N-(6-aminohexyl)-N-propyl-5-isoquinolinesulfonamide
(11) N-(2-aminopropyl)-N-hexyl-5-isoquinolinesulfonamide
(12) N-(2-aminobutyl)-N-hexyl-5-isoquinolinesulfonamide
(13) N-(2-aminooctyl)-N-hexyl-5-isoquinolinesulfonamide
(14) N-(2-aminodecyl)-N-propyl-5-isoquinolinesulfonamide
(15) N-(2-aminodecyl)-N-hexyl-5-isoquinolinesulfonamide
(16) N-(2-amino-1-methylpropyl)-N-butyl-5-isoquinolinesulfonamide
(17) N-(2-amino-1-methylethyl)-N-ethyl-5-isoquinolinesulfonamide
(18) N-(1-aminomethyl-2-methylpropyl)-N-propyl-5-isoquinolinesulfonamide
(19) N-(1-aminomethylpentyl)-N-hexyl-5-isoquinolinesulfonamidesulfonamide
(20) N-(3-amino-2-methylpropyl)-N-propyl-5-isoquinolinesulfonamide
(21) N-(4-amino-1-methylbutyl)-N-hexyl-5-isoquinolinesulfonamidesulfonamide
(22) N-(5-aminomethylhexyl)-N-ethyl-5-isoquinolinesulfonamidesulfonamide
(23) N-(4-amino-3-methylbutyl)-N-hexyl-5-isoquinolinesulfonamidesulfonamide
(24) N-(4-amino-1-propylbutyl)-N-hexyl-5-isoquinolinesulfonamidesulfonamide
(25) N-(2-methylaminoethyl)-N-methyl-5-isoquinolinesulfonamide
(26) N-(2-ethylaminoethyl)-N-ethyl-5-isoquinolinesulfonamidesulfonamide
(27) N-(2-butylaminoethyl)-N-hexyl-5-isoquinolinesulfonamidesulfonamide
(28) N-ethyl-N-(2-hexylaminoethyl)-5-isoquinolinesulfonamidesulfonamide
(29) N-(2-hexylaminoethyl)-N-hexyl-5-isoquinolinesulfonamidesulfonamide
(30) N-(2-benzylaminoethyl)-N-benzyl-5-isoquinolinesulfonamidesulfonamide
(31) N-butyl-N-(2-phenylethylaminoethyl)-5-isoquinolinesulfonamide
(32) N-(2-benzylaminoethyl)-N-hexyl-5-isoquinolinesulfonamidesulfonamide
(33) N-(3-hexylaminopropyl)-N-hexyl-5-isoquinolinesulfonamidesulfonamide
(34) N-(6-benzylaminohexyl)-N-pentyl-5-isoquinolinesulfonamidesulfonamide
(35) N-(6-hexylaminohexyl)-N-hexyl-5-isoquinolinesulfonamidesulfonamide
(36) N-(2-ethylaminopropyl)-N-hexyl-5-isoquinolinesulfonamidesulfonamide
(37) N-(2-hexylaminopropyl)-N-hexyl-5-isoquinolinesulfonamidesulfonamide
(38) N-(2-propylaminooctyl)-N-butyl-5-isoquinolinesulfonamidesulfonamide
(39) N-hexyl-N-(2-isopropylamino-1-methylethyl)-5-isoquinolinesulfonamide
(40) N-(4-benzylamino-1-methylbutyl)-N-propyl-5-isoquinolinesulfonamide
(41) N-methyl-N-(6-propylamino-5-methylhexyl)-5-isoquinolinesulfonamide
(42) N-(2-diethylaminoethyl)-N-methyl-5-isoquinolinesulfonamidesulfonamide
(43) N-(2-dimethylaminoethyl)-N-hexyl-5-isoquinolinesulfonamidesulfonamide
(44) N-benzyl-N-(2-dihexylaminoethyl)-5-isoquinolinesulfonamidesulfonamide
(45) N-hexyl-N-(2-piperidinoethyl)-5-isoquinolinesulfonamide
(46) N-hexyl-N-(2-morpholinoethyl)-5-isoquinolinesulfonamide
(47) N-[2-(N-cyclohexyl-N-methylamino)ethyl]-N-ethyl-5-isoquinolinesulfonamide
(48) N-hexyl-N-(2-piperidinopropyl)-5-isoquinolinesulfonamide
(49) N-(2-diethylamino-1-methylethyl)-N-hexyl-5-isoquinolinesulfonamide

(50) N-ethyl-N-(5-piperidinopentyl)-5-isoquinolinesulfonamide
(51) 1-(5-isoquinolinesulfonyl)-4-aminopiperidine
(52) 1-(5-isoquinolinesulfonyl)-4-methylaminopiperidine
(53) 1-(5-isoquinolinesulfonyl)-4-ethylaminopiperidine
(54) 1-(5-isoquinolinesulfonyl)-4-propylaminopiperidine
(55) 1-(5-isoquinolinesulfonyl)-4-isopropylaminopiperidine
(56) 1-(5-isoquinolinesulfonyl)-4-butylaminopiperidine
(57) 1-(5-isoquinolinesulfonyl)-4-hexlaminopiperidine
(58) 1-(5-isoquinolinesulfonyl)-4-phenylaminopiperidine
(59) 1-(5-isoquinolinesulfonyl)-4-(N-hexyl-N-methylamino)piperidine
(60) 1-(5-isoquinolinesulfonyl)-4-benzylaminopiperidine
(61) 1-(5-isoquinolinesulfonyl)-4-phenethylaminopiperidine
(62) 1-(5-isoquinolinesulfonyl)-4-piperidinopiperidine
(63) 1-(5-isoquinolinesulfonyl)-3-aminopiperidine
(64) 1-(5-isoquinolinesulfonyl)-3-methylaminopiperidine
(65) 1-(5-isoquinolinesulfonyl)-3-ethylaminopiperidine
(66) 1-(5-isoquinolinesulfonyl)-3-propylaminopiperidine
(67) 1-(5-isoquinolinesulfonyl)-3-isopropylaminopiperidine
(68) 1-(5-isoquinolinesulfonyl)-3-phenylaminopiperidine
(69) 1-(5-isoquinolinesulfonyl)-3-benzylaminopiperidine
(70) 1-(5-isoquinolinesulfonyl)-3-phenethylaminopiperidine
(71) 1-(5-isoquinolinesulfonyl)-3-hexylaminopiperidine
(72) 1-(5-isoquinolinesulfonyl)-3-piperidinopiperidine
(73) 1-(5-isoquinolinesulfonyl)-3-dimethylaminopiperidine
(74) 1-(5-isoquinolinesulfonyl)-3-amino-2-methylpiperidine
(75) 1-(5-isoquinolinesulfonyl)-3-amino-4-methylpiperidine
(76) 1-(5-isoquinolinesulfonyl)-3-methylaminopyrrolidine
(77) 1-(5-isoquinolinesulfonyl)-3-amino-5-methylpyrrolidine
(78) 1-(5-isoquinolinesulfonyl)-3-aminopyrrolidine
(79) 1-(1-hydroxy-5-isoquinolinesulfonyl)-4-aminopiperidine
(80) 1-(1-hydroxy-5-isoquinolinesulfonyl)-4-methylaminopiperidine
(81) 1-(1-hydroxy-5-isoquinolinesulfonyl)-4-propylaminopiperidine
(82) 1-(1-hydroxy-5-isoquinolinesulfonyl)-4-phenylaminopiperidine
(83) 1-(1-hydroxy-5-isoquinolinesulfonyl)-4-benzylaminopiperidine
(84) 1-(1-hydroxy-5-isoquinolinesulfonyl)-3-aminopiperidine
(85) 1-(1-hydroxy-5-isoqyubikubesykfibtk)-3-propylaminopiperidine
(86) 1-(1-hydroxy-5-isoquinolinesulfonyl)-3-benzylaminopiperidine
(87) 1-(1-hydroxy-5-isoquinolinesulfonyl)-3-phenylaminopiperidine
(88) 1-(1-hydroxy-5-isoquinolinesulfonyl)-3-hexylaminopiperidine
(89) 1-(1-hydroxy-5-isoquinolinesulfonyl)-3-phenethylaminopiperidine
(90) 1-(1-hydroxy-5-isoquinolinesulfonyl)-3-dimethylaminopiperidine
(91) 1-(1-hydroxy-5-isoquinolinesulfonyl)-3-amino-5-methylpiperidine
(92) 1-(1-hydroxy-5-isoquinolinesulfonyl)-3-aminopyrrolidine
(93) 1-(1-hydroxy-5-isoquinolinesulfonyl)-3-methylaminopyrrolidine
(94) 1-(1-chloro-5-isoquinolinesulfonyl)-4-methylaminopiperidine
(95) 1-(1-chloro-5-isoquinolinesulfonyl)-4-benzylaminopipepridine
(96) 1-(1-chloro-5-isoquinolinesulfonyl)-3-aminopiperidine
(97) 1-(1-chloro-5-isoquinolinesulfonyl)-3-ethylaminopiperidine
(98) 1-(1-chloro-5-isoquinolinesulfonyl)-3-hexylaminopiperidine
(99) 1-(1-chloro-5-isoquinolinesulfonyl)-3-dimethylaminopiperidine
(100) 1-(1-chloro-5-isoquinolinesulfonyl)-3-(N-hexyl-N-methylamino)piperidine
(101) 1-(1-chloro-5-isoquinolinesulfonyl)-3-aminopyrrolidine
(102) 1-(1-chloro-5-isoquinolinesulfonyl)-3-methylaminopyrrolidine.

The acid salts of the isoquinoline derivatives of formula (I) are pharmacologically acceptable non-toxic salts. As examples of the acid, there may be mentioned such inorganic acids as hydrochloric acid, hydrobromic acid, phosphoric acid and sulfuric acid and such organic acids as acetic acid, citric acid, tartaric acid, lactic acid, succinic acid, fumaric acid, maleic acid and methanesulfonic acid.

The compound of formula (I) according to the present invention may be prepared, for example, from 5-isoquinolinesulfonyl chloride or 1-chloro-5-isoquinolinesulfonyl chloride, or acid salts thereof.

5-Isoquinolinesulfonyl chloride or 1-chloro-5-isoquinolinesulfonyl chloride, which are known compounds, may be prepared by reacting 5-isoquinolinesulfonic acid or 1-chloro-5-isoquinolinesulfonic acid with thionyl chloride in the presence of N,N-dimethylformamide as catalyst.

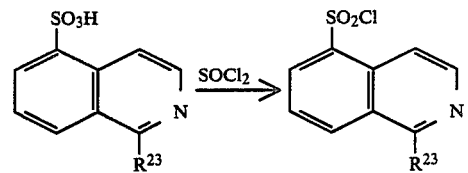

wherein $R^{23}$ is a hydrogen atom or a chlorine atom. The amount of thionyl chloride may be in the range of from 3 to 10 parts by weight per part by weight of 5-isoquinolinesulfonic acid or 1-chloro-5-isoquinolinesulfonic acid. The amount of N,N-dimethylformamide may be in the range of from 0.5 to 10% by weight based on the thionyl chloride. The reaction may be carried out at 40° to 80° C. for 0.5 to 8 hours to obtain the desired compound.

Using 5-isoquinolinesulfonyl chloride or 1-chloro-5-isoquinolinesulfonyl chloride or an acid salt thereof as a starting material, the compound of formula (I) according to the present invention may be prepared, for example, by any of the following Methods A to D.

COMPOUNDS OF FORMULA (I) WHEREIN R¹ IS A HYDROGEN ATOM OR A CHLORINE ATOM

Method A

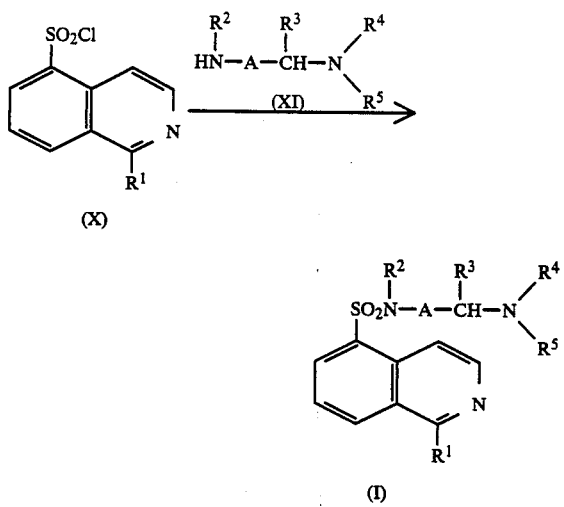

wherein A, $R^2$, $R^3$, $R^4$ and $R^5$ are as defined above, and $R^1$ is a hydrogen atom or a chlorine atom.

The compound of formula (X) is reacted with a compound represented by the formula (XI) to obtain a compound of the present invention represented by the formula (I) wherein $R^1$ is a hydrogen or a chlorine atom.

Examples of the compound of formula (XI) include N,N'-trimethylethylenediamine, N,N'-triethylethylenediamine, N-diethyl-N'-methylethylenediamine, N-dimethyl-N'-hexylethylenediamine, N-benzyl-N'-dihexylethylenediamine, N-hexyl-2-piperidinoethylamine, N-hexyl-2-morpholinoethylamine, N-cyclohexyl-N-methyl-N'-ethylethylenediamine, N-hexyl-2-piperidinopropylamine, 2-diethylamino-N-hexyl-1-methylethylamine, N-ethyl-5-piperidinopentylamine, 4-aminopiperidine, 4-methylaminopiperidine, 4-ethylaminopiperidine, 4-propylaminopiperidine, 4-isopropylaminopiperidine, 4-butylaminopiperidine, 4-hexylaminopiperidine, 4-phenylaminopiperidine, 4-(N-hexyl-N-methylamino)piperidine, 4-benzylaminopiperidine, 4-phenethylaminopiperidine, 4-piperidinopiperidine, 3-aminopiperidine, 3-methylaminopiperidine, 3-ethylaminopiperidine, 3-propylaminopiperidine, 3-isopropylaminopiperidine, 3-phenylaminopiperidine, 3-benzylaminopiperidine, 3-phenethylaminopiperidine, 3-piperidinopiperidine, 3-dimethylaminopiperidine, 3-amino-4-methylpiperidine, 3-aminopyrrolidine and 3-methylaminopyrrolidine.

The reaction between the compound of formula (X) and the compound of formula (XI) preferably is carried out in the presence or absence of an acid acceptor. The use of an acid acceptor is preferred since, as explained later, it enables the necessary amount of the compound (XI), which is expensive, to be decreased. Examples of acid acceptors which may be employed include alkali metal compounds such as sodium hydrogencarbonate, sodium hydroxide, potassium carbonate, sodium carbonate, potassium hydroxide and sodium methylate, and organic tertiary amines such as pyridine, trimethylamine and triethylamine.

In general, this reaction is carried out in a reaction medium. Examples of reaction media which may be employed include alcohols such as methanol, ethanol and butanol; halogenated hydrocarbons such as dichloromethane and chloroform; ethers such as tetrahydrofuran, dioxane and diethyl ether; dimethyl sulfoxide; N,N-dimethylformamide; acetonitrile; and water. The reaction media used may be a single compound or a combination of two or more compounds. The amount of the reaction medium may be in the range of from 3 to 100 ml per gram of the compound of formula (XI).

The amount of the compound of formula (XI) may be in the range of from 1 to 20 mols, preferably from 1 to 10 mols per mol of the compound of formula (X). A more preferred amount of the compound of formula (XI) may be in the range of from 2.5 to 5 mols per mol of the compound of formula (X) when an acid acceptor is absent, and of from 1 to 3 mols per mol of the compound of formula (X) when an acid acceptor is present.

When an acid acceptor is employed, its amount may be in the range of from 1 to 10 mols, preferably 1 to 6 mols per mol of the Compound of the formula (XI).

The reaction temperature in the reaction between the compound of formula (X) and the compound of formula (XI) may generally be in the range of from −30° to 120° C., preferably −20° to 50° C. The reaction time which may be employed is generally 0.5 to 48 hours preferably 0.5 to 6 hours.

Method B

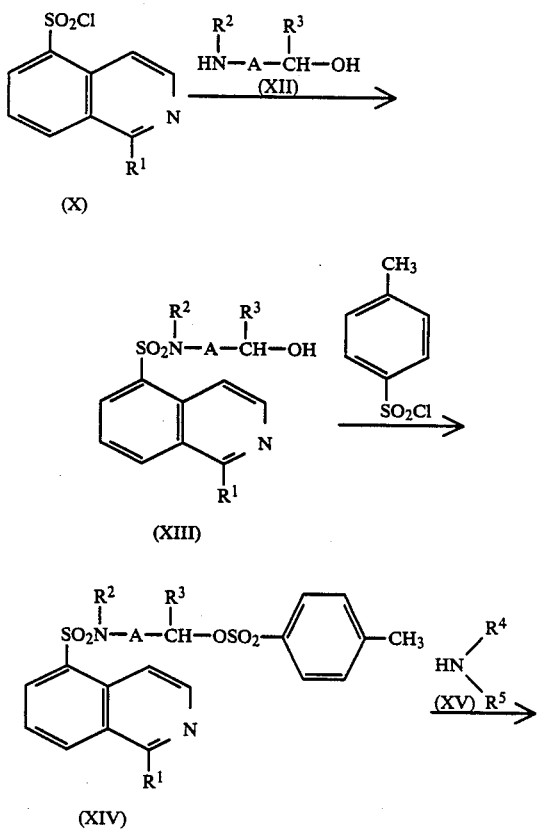

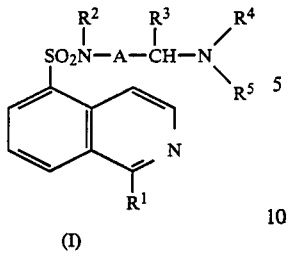

(I)

wherein A, $R^2$, $R^3$, $R^4$ and $R^5$ are as defined above, and $R^1$ is a hydrogen atom or a chlorine atom.

At the first step, the compound of formula (X) is reacted with a compound represented by the formula (XII) to obtain a compound represented by the formula (XIII).

Examples of the compound of formula (XII) include 2-methylaminoethanol, 2-ethylaminoethanol, 2-isopropylaminoethanol, 2-butylaminoethanol, 2-hexylaminoethanol, 2-octylaminoethanol, 2-benzylaminoethanol, 3-hexylamino-1-propanol, 4-hexylamino-1-butanol, 5-hexylamilno-1-pentanol, 6-propylamino-1-hexanol, 1-hexylamino-2-propanol, 1-hexylamino-2-butanol, 1-hexylamilno-2-octanol, 1-propylamino-2-decanol, 1-hexylamino-2-decanol, 2-butylamino-1-methyl-1-propanol, 2-ethylamino-1-propanol, 2-propylamino-3-methyl-1-butanol, 2-hexylamino-1-hexanol, 3-propylamino-2-methyl-1-propanol, 4-hexylamino-1-pentanol, 6-ethylamino-2-hexanol, 4-hexylamino-2-methyl- 1-butanol, 6-hexylamino-2-nonanol, 3-hydroxypiperidine, 4-hydroxypiperidine, 3-hydroxy-5-methylpiperidine, 3-hydroxy-4-methylpiperidine, 3-aminopyrrolidine and 3-hydroxy-5-methylpyrrolidine.

The reaction between the compound of formula (X) and the compound of formula (XII) may be carried out in the presence or absence of an acid acceptor. However, the use of an acid acceptor is preferred since, as explained later, it enables the necessary amount of the compound of (XII) to be decreased. Examples of acid acceptors which can be employed include alkali metal compounds such as sodium hydrogencarbonate, sodium hydroxide, potassium carbonate, sodium carbonate, potassium hydroxide and sodium methylate, and organic tertiary amines such as pyridine, trimethylamine and triethylamine.

In general, this reaction may be carried out in a reaction medium. Examples of reaction media which can be employed include alcohols such as methanol, ethanol and butanol; halogenated hydrocarbons such as dichloromethane and chloroform; ethers such as tetrahydrofuran, dioxane and diethyl ether; dimethyl sulfoxide; N,N-dimethylformamide; acetonitrile; and water. The reaction media may be a single compound or a combination of two or more compounds. The amount of the reaction medium may be in the range of from 3 to 100 ml per gram of the compound of formula (XII).

The amount of the compound of formula (XII) may generally be in the range of from 1 to 20 mols, preferably from 1 to 10 mols per mol of the compound of formula (X). A more preferred amount of the compound of formula (XII) ranges from 2.5 to 5 mols per mol of the compound of formula (X) when an acid acceptor is absent, and from 1 to 3 mols per mol of the compound of formula (X) when an acid acceptor is present.

When an acid acceptor is employed, its amount may be in the range of from 1 to 10 mols, preferably 1 to 6 mols per mol of the compound of formula (XII).

The reaction temperature in the reaction between the compound of formula (X) and the compound of formula (XII) may generally be in the range of from −30° to 120° C., preferably −20° to 50° C. The reaction time which can be employed may generally be in the range of from 0.5 to 48 hours, preferably 0.5 to 6 hours.

At the second step, the compound of formula (XIII) is reacted with p-toluenesulfonyl chloride to obtain a compound represented by the formula (XIV). This reaction may be conducted according to a method described in L. F. Fieser and M. Fieser, "Reagents for Organic Synthesis", collective vol. I, 1180 (1967). For example, the compound of formula (XIII) is dissolved in pyridine, and to the resultant solution is added p-toluenesulfonl chloride in an amount of 1 to 2 mols per mol of the compound of formula (XIII). The reaction is allowed to proceed preferably at 10° to 80° C. for 2 to 48 hours, whereby the compound of formula (XIV) is obtained in high yield.

Finally, the compound of formula (XIV) is reacted with ammonia or an amine represented by the formula (XV) to obtain a compound of the present invention represented by the formula (I) wherein $R^1$ is a hydrogen or a chlorine atom.

Examples of the compound of formula (XV) include ammonia, methylamine, dimethylamine, ethylamine, propylamine, isopropylamine, butylamine, hexylamine, piperidine, benzylamine and phenethylamine. The amount of the compound of formula (XV) may be in the range of from 1 to 50 mols per mol of the compound of formula (XIV). This reaction may preferably be conducted in a sealed vessel, since the boiling points of the compounds of formula (XV) are low.

In general, this reaction is carried out in a reaction medium. Examples of reaction media which can be employed include alcohols such as methanol, ethanol and butanol; halogenated hydrocarbons such as dichloromethane and chloroform; and ethers such as tetrahydrofuran, dioxane and diethyl ether. The reaction media may be a single compound or a combination of two or more compounds. The amount of the reaction medium may be in the range of from 3 to 100 ml per gram of the compound of formula (XV).

The reaction temperature in the reaction between the compound of formula (XIV) and the compound of formula (XV) may be in the range of from 10° to 120° C., preferably 60° to 110° C. The reaction time which can be employed may be 0.5 to 72 hours.

Method C

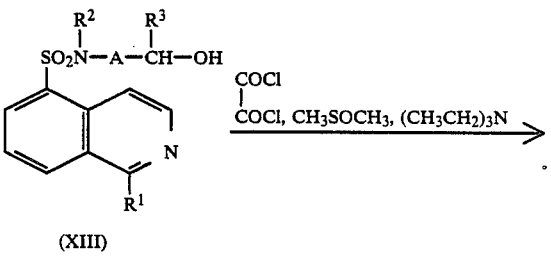

(XIII)

-continued

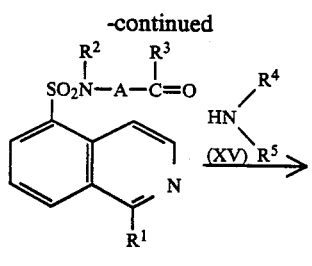
(XVI)

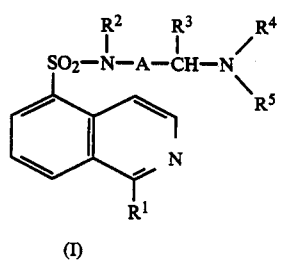
(I)

wherein A, R², R³, R⁴ and R⁵ are as defined above, and R¹ is a hydrogen atom or a chlorine atom.

The compound of formula (XIII), obtained as in Method B, is reacted first with oxalyl chloride and dimethylsulfoxide and then with triethylamine to obtain a compound represented by the formula (XVI).

This reaction may be conducted according to a method described in "Journal of Organic Chemistry", vol 43, 2480 (1978). For example, equimolar amounts of oxalyl chloride and dimethylsulfoxide are mixed in methylene chloride at −50° to −70° C. To the resultant solution, a methylene chloride solution containing 10 to 50 w/v % of the compound of formula (XIII) is added dropwise in an equimolar amount, in terms of the compound (XIII), relative to the amount of each of the oxalyl chloride and dimethylsulfoxide. The reaction is allowed to proceed at −50° to −70° C. for 0.5 to 1 hour. To the resultant solution is added triethylamine in an equimolar amount relative to the compound of formula (XIII), and the reaction is allowed to proceed at −50° to −70° C. for 5 to 30 minutes, thereby to obtain the compound of formula (XVI).

Next, the compound of formula (XVI) is reacted with ammonia or an amine represented by the formula (XV) in the presence of sodium cyanoborohydride to obtain a compound of the present invention represented by the formula (I) wherein R¹ is a hydrogen or a chlorine atom. This reaction may be conducted according to a method described in "Journal of American Chemical Society", vol 93, 2897 (1971).

Examples of the compound of formula (XV) include ammonia, methylamine, dimethylamine, ethylamine, propylamine, isopropylamine, butylamine, hexylamine, piperidine, benzylamine and phenethylamine. Preferably, these compounds are employed in the form of acid salts, such as a hydrochloride, a sulfate, an acetate and the like. That is, for example, when ammonia is employed as the compound of formula (XV), its preferred form is ammonium acetate, ammonium hydrochloride, ammonium sulfate and the like. The amount of the compound of formula (XV) may be in the range of from 1 to 10 mols per mol of the compound of formula (XVI).

The amount of sodium cyanoborohydride employed may generally be in the range of from 0.5 to 10 mols, preferably 0.5 to 5 mols, more preferably 0.7 to 2 mols per mol of the compound of formula (XVI).

In general, the reaction may be carried out in a reaction medium. Examples of reaction medium which can be employed include alcohols such as methanol, ethanol and butanol and water. The reaction media may be a single compound or a combination of compounds. The amount of the reaction medium may be in the range of from 3 to 100 ml per gram of the compound of formula (XV).

The reaction temperature in the reaction between the compound of formula (XVI) and the compound of formula (XV) may generally be in the range of from −30° to 120° C., preferably 0° to 70° C., more preferably 10° to 50° C. The reaction time which can be employed may generally be 1 to 96 hours, preferably 4 to 24 hours.

COMPOUNDS OF FORMULA (I) WHEREIN R¹ IS A HYDROXYL GROUP

Method D

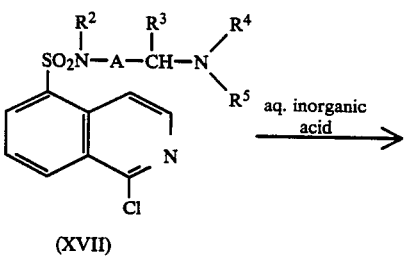
(XVII)

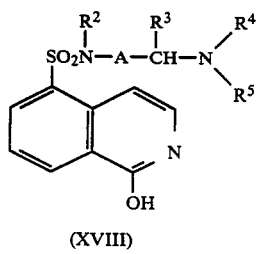
(XVIII)

wherein A, R⁴ and R⁵ are as defined above, and R² and R³ are directly bonded with each other to form an ethylene or trimethylene group which is unsubstituted or substitued with an alkyl group having 1 to 8 carbon atoms.

In this method, a compound represented by the formula (XVII) wherein R¹ is a chlorine atom, which is one of the compounds of the present invention and can be obtained by any of the above-mentioned Methods A to C, is treated with an aqueous inorganic acid solution to obtain a compound of the present invention represented by the formula (XVIII).

Examples of the inorganic acid include hydrochloric acid, sulfuric acid and nitric acid. The concentration of the inorganic acid in the aqueous solution may be 0.25 to 10 mol/liter. The reaction may be performed at 50° to 100° C. for 2 to 6 hours.

Acid salts of the compounds of formula (I) may be prepared, for example, by the following method.

The compound of formula (I) is dissolved in a reaction medium to obtain a solution. Examples of the reaction medium include alcohols such as methanol and ethanol and water. The concentration of the compound (I) in the solution is not critical, but generally it may be in the range of from 5 to 20 w/v %. Subsequently, an acid is added to and dissolved in the solution. Examples of suitable acids include inorganic acids such as hydrochloric acid, hydrobromic acid, phosphoric acid and sulfuric acid and organic acids such as acetic acid, citric acid, tartaric acid, lactic acid, succinic acid, fumaric acid, maleic acid and methanesulfonic acid. The amount of the acid is not critical, but it may preferably be in the range of from 1.0 to 1.2 mols per mol of the compound (I).

The solution thus prepared is subjected to vacuum concentration, lyophilization or the like to obtain a residue. The residue is purified by, for example, recrystalization with methanol, ethanol or the like to obtain an acid salt of the compound of formula (I).

The isoquinoline derivative represented by the formula (I) and the pharmacologically acceptable acid salt thereof according to the present invention can effectively increase the diameter of blood vessels, especially a coronary artery, and exert an excellent relaxation action on the smooth muscle of a blood vessel, an excellent blood flow increasing action and an antihypertensive acion. Hence, they can be advantageously utilized as vasodilators, cerebral circulation ameliorators and drugs for the prevention and treatment of angina, myocardial infarction, cerebrovascular thrombosis, cardiovascular thrombosis, hypertonia, and other circulatory organ diseases. Moreover, the compounds of the present invention also exert an excellent smooth muscle relaxation action on bronchial tubes, which action is not exerted by known cerebrovascular compounds. Accordingly, these compounds are also valuable drugs for the prevention and treatment of respiratory organ diseases such as asthma.

The above-mentioned relaxation action on the smooth muscle of a blood vessel was confirmed by the relaxation of the mesenteric artery of a rabbit in accordance with the method described later. The above-mentioned blood flow increasing action was confirmed by the increase in blood flow of dog's vertebral, coronary and femoral arteries in accordance with the method described later. The above-mentioned relaxation action on bronchial tubes was confirmed through the histamine contraction inhibition action on bronchial tubes removed from a guinea pig.

The acute toxicity of the compounds of the present invention was determined according to the method given later, and the results are shown in Table 17. For example, N-(2-aminoethyl)-N-hexyl-5-isoquinolinesulfonamide [Compound (4)] and 1-(5-isoquinolinesulfonyl)-3-aminopiperidine [Compound (63)] exhibited $LD_{50}$ values of 95 mg/kg and 176 mg/kg, respectively. These results show that the acute toxicity of the compounds of the present invention is sufficiently low to safely permit their use as drugs.

Particulary, with respect to the increased blood flow action, the compounds of the present invention selectively act on a coronary artery as compared with the known compounds. This will be demonstrated in Application Example 2 given later in which the compounds of the present invention were intravenously administered to dogs and the change in blood flow was measured. For example, N-(2-aminoethyl)-N-hexyl-5-isoquinolinesulfonamide [Compound (4)] elicited, at a dose of 0.3 mg/kg, 188% and 170% augmentation in blood flow through the coronary and vertebral arteries; and 1-(5-isoquinolinesulfonyl)-3-aminopiperidine [Compound (63)] elicited, at a dose of 1.0 mg/kg, 128% and 95% augmentation in blood flow through the coronary and vertebral arteries. On the other hand, the known compound 1-(5-isoquinolinesulfonyl)homopiperazine elicited, at a dose of 0.3 mg/kg, 160% augmentation in blood flow through the vertebral artery. However, the blood flow augmentation through the coronary artery was only 89%, which is very low compared with the 160% augmentation for the vertebral artery. As is apparent from these results, the compounds of the present invention can be more advantageously utilized as drugs for coronary vessel diseases than the known compound.

Further, with respect to the relaxation action on bronchial tubes, Application Example 3 given later shows that the strong action is exerted by the compounds of the present invention. For example, in the histamine contraction inhibition test using bronchial tube samples from a guinea pig, 1-(5-isoquinolinesulfonyl)-3-aminopiperidine [Compound (63)] exhibited $ED_{50}$ value, i.e. a concentration which attains 50% relaxation, of 3 $\mu M$. This strong relaxation action on bronchial tubes shows that the compounds of the present invention are also useful as drugs for the prevention and treatment of respiratory organ diseases such as asthma.

The compounds of the present invention may be formulated into a pharmaceutical composition by admixing a compound of the formula (I) or its acid salt as an essential active component with a pharmaceutically acceptable non-toxic carrier.

The compounds of the present invention may be administered to humans as an oral drug or by intravenous injection in the case of circulatory organ diseases, or they may be administered as an oral drug or an inhalant or by intravenous injection in the case of respiratory organ diseases. The dose may generally be 15 to 300 mg per day for an adult. The daily administration may be effected at a single time or effected in multiple doses such as 2 to 3 times a day, and continued for a period of from several days to 2 months. The dose and the administration duration vary to some extent depending on the condition of the patient.

Still further, the compound of the present invention may be used in combination with other drugs, depending on the condition of the patient. For example, for the treatment of circulatory organ diseases, the compound may be used in combination with a diuretic, an antihypertensive agent, a $\beta$-blocker, a platelet agglutination inhibitor, a thrombolytic drug, etc. For the treatment of respiratory organ diseases, the compound may be used in combination with a cerebral metabolism ameliorator etc.

DETAILED DESCRIPTION OF THE PREFERRED EMBODIMENT

This invention will now be described in detail with reference to the following Examples and Application Examples but they should not be construed to be limiting the scope of the present invention. In the Application Examples 1 to 4, the effects of the compounds of the present invention were examined according to the methods given below.

1. Relaxation of Mesenteric Artery

A rabbit of Japanese local variety weighing about 3 kg was bled to death. Then, the abdomen of the rabbit was dissected to locate a mesenteric artery. According to the customary method, the artery was cut into a spiral having a width of 2 mm and a length of 25 mm, and suspended in a 20-ml organ bath filled with Krebs-Henseleit nutrient solution through which a gas mixture consisting of 95% by volume of $O_2$ and 5% by volume of $CO_2$ had been bubbled. The free end of the suspended artery was connected to an isometric transducer (FD Pickup TB-912T, trade name of NIHON KODEN CO., LTD.) and tensioned at a load of 1.5 g. Thus, shrinking and relaxation of the artery could be measured as a load on the transducer. To the organ bath, KCl was added so that the KCl concentration became 15 to 20 mM, causing the artery to shrink. Then, the compounds of the present invention were added to the organ bath to observe relaxation of the artery. Measurement was made of concentrations ($ED_{50}$) of the compounds which attained 50% of complete relaxation.

2. Blood Flow Increase of Coronary, Vertebral and Femoral Arteries

Mongrel dogs weighing 8 to 15 kg were put under anesthesia by intravenously administering pentobarbital in a dose of 35 mg/kg. A plethysmographic probe (manufactured and sold by NIHON KODEN CO., LTD., Japan) was mounted on the coronary, vertebral and femoral arteries, and blood flow was measured by means of an electromagnetic blood flowmeter (type:MF-27, manufactured and sold by NIHON KODEN CO., LTD., Japan). Under these conditions, the compounds of the present invention were intravenously administered through a polyethylene tube inserted to a femoral veinlet, and the change in blood flow was measured for 30 minutes by means of the electromagnetic blood flowmeter.

3. Inhibition of Histamine Contraction of Bronchial Tubes (Relaxation of Bronchial Tubes)

The relaxation action of the compounds of the present invention on the smooth muscle of bronchial tubes was examined by means of Magnus apparatus according to the "Method Of Using Bronchial Tubes Taken Out From Guinea Pigs" (K. Takagi and H. Ozawa, "Experimental Techniques in Pharmacology", p100-102 (1960), NANZANDO CO., LTD.; M. Fujiwara and S. Shibata "Basic Experimental Methods of Pharmacology" p131-134 (1982), KYORINSHOIN CO., LTD.). That is, a bronchial tube sample taken from a guinea pig was suspended in the 20-ml bath filled with Krebs-Henseleit nutrient solution and maintained at a temperature of 37° C. To the bath was added histamine so that the histamine concentration became 10 μM, causing the bronchial tube sample to contract. After the contraction became stable, the compounds of the present invention were added cumulatively to the bath to observe relaxation of the bronchial tube sample. Measurement was made of concentrations ($ED_{50}$) of the compounds which attained 50% decrease of the contraction caused by 10 μM histamine.

4. Acute Toxicity

Using ddY male mice and Wistar male rats, the acute toxicity of the compounds of the present invention was examined with respect to $LD_{50}$ according to the method proposed by K. Takagi et al. (K. Takagi and H. Ozawa, "Expeprimental Techniques in Pharmacology," p200-206 (1960), NANZANDO CO., LTD., Japan).

EXAMPLE 1

In 50 ml of ice water was dissolved 5.3 g of 5-isoquinolinesulfonyl chloride hydrochloride, and the pH of the solution was adjusted to 6 with a saturated aqueous sodium hydrogencarbonate solution, followed by extraction with 100 ml of dichloromethane. The dichloromethane layer was added dropwise to a 50 ml of dichloromethane solution containing 6.0 g of 3-aminopiperidine over 20 minutes while cooling with ice. The mixture was stirred at a temperature of 15° C. to 20° C. for 2 hours, washed with water, and dried with anhydrous magnesium sulfate. Then, the dichloromethane was removed under reduced pressure to obtain an oily residue. The thus obtained oily residue was subjected to purification by silica gel column chromatography (Wacogel C-200, 200 g; solvent: chloroform) to obtain 5.32 g of 1-(5-iso-quinolinesulfonyl)-3-aminopiperidine [Compound (63)] in a yield of 91%. Compound (63) was analyzed to give the following data.

IR absorption spectrum (cm$^{-1}$): 2950, 1340, 1160.

NMR spectrum (CD$_3$OD-DCl): 0.8-2.0(4H), 2.1-3.2 (3H), 3.3-3.8(2H), 7.4-7.9(1H), 8.0-8.7(4H), 9.3(1H).

Substantially the same procedures as described above were repeated except that each of the compounds of the formula (XI) as indicated in Table 1-1 was used in place of 3-aminopiperidine and that the reaction conditions were changed as indicated in Table 1-1. There were obtained 1-(5-isoquinolinesulfonyl)-4-phenylaminopiperidine [Compound (58)], 1-(5-isoquinolinesulfonyl)-4-(N-hexyl-N-methylamino)-piperidine [Compound (59)], 1-(5-isoquinolinesulfonyl)-3-phenylaminopiperidine [Compound (68)], 1-(5-isoquinolinesulfonyl)-3-dimethylaminopiperidine [Compound (73)] and 1-(5-isoquinolinesulfonyl)-3-amino-4-methylpiperidine [Compound (75)]. The yields and analytical values of these compounds are shown on Table 1-2.

EXAMPLE 2

In 30 ml of ice water was dissolved 3.0 g of 1-chloro-5-isoquinolinesulfonyl chloride hydrochloride, and the pH of the solution was adjusted to 6 with a saturated aqueous sodium hydrogencarbonate solution, followed by extraction with 50 ml of dichloromethane.

TABLE 1

| Run No. | 5-Isoquinoline-sulfonyl chloride hydrochloride (g) | Compound (XI) | (g) | Reaction temperature (°C.) | Reaction time (hr) | Obtained compound | Yield | IR spectrum (cm$^{-1}$) | NMR spectrum (CD$_3$OD-DCl) |
|---|---|---|---|---|---|---|---|---|---|
| 1-1 | 1.3 | HN—(piperidine)—NHC$_6$H$_5$ | 2.6 | 10–20 | 2 | (58) | 1.17 g (64%) | 2950, 1340 1160 | 0.8-2.1(4H), 2.3-4.1(5H) 7.4-7.9(6H), 8.0-8.7(4H) 9.1-9.3(1H) |
| 1-2 | 1.3 | HN—(piperidine)—N(C$_6$H$_{13}$)(CH$_3$) | 3.0 | 10–20 | 2 | (59) | 1.54 g (79%) | 2950, 1340 1160 | 0.8-3.2(22H), 3.7-4.1(3H) 7.4-7.9(1H), 8.0-8.7(4H) 9.1-9.3(1H) |

TABLE 1-continued

| Run No. | 5-Isoquinoline-sulfonyl chloride hydrochloride (g) | Compound (XI) | (g) | Reaction temperature (°C.) | Reaction time (hr) | Obtained compound | Yield | IR spectrum (cm$^{-1}$) | NMR spectrum (CD$_3$OD-DCl) |
|---|---|---|---|---|---|---|---|---|---|
| 1-3 | 1.3 | (piperidine-NHC$_6$H$_5$) | 2.6 | 10–20 | 2 | (68) | 1.34 g (73%) | 2950, 1340 1160 | 0.8–2.0(4H), 2.1–3.2(3H) 3.3–3.8(2H), 7.4–7.9(6H) 8.0–8.7(4H), 9.1–9.3(1H) |
| 1-4 | 1.3 | (piperidine-NMe$_2$) | 2.0 | 10–20 | 15 | (73) | 1.31 g (82%) | 2950, 1340 1160 | 0.6–3.2(10H), 3.2–3.8(5H) 7.4–7.9(1H), 8.0–8.7(4H) 9.1–9.3(1H) |
| 1-5 | 1.3 | (piperidine-CH$_3$,NH$_2$) | 1.7 | 15–20 | 15 | (75) | 0.87 g (57%) | 2950, 1340 1160 | 0.6–2.0(5H), 2.1–3.8(6H) 7.4–7.9(1H), 8.0–8.7(4H) 9.1–9.3(1H) |

The dichloromethane layer was added dropwise to a 50 ml of dichloromethane solution containing 3.0 g of 3-aminopiperidine over 20 minutes while cooling with ice. The mixture was stirred at a temperature of 15° C. to 20° C. for 2 hours, washed with water, and dried with anhydrous magnesium sulfate. Then, the dichloromethane was removed under reduced pressure to obtain an oily residue. The thus obtained oily residue was subjected to purification by silica gel column chromatography (Wacogel C-200, 200 g; solvent:chloroform) to obtain 2.73 g of 1-(1-chloro-5-isoquinolinesulfonyl)-3-aminopiperidine [Compound (96)] in a yield of 84%. Compound (96) was analyzed to give the following data.

IR absorption spectrum (cm$^{-1}$): 2950, 1340, 1160.
NMR spectrum (CD$_3$OD-DCl): 0.8–2.0(4H), 2.1–3.2(3H), 3.3–3.8(2H), 7.4–7.9(1H), 8.0–8.7(4H).

Substantially the same procedures as described above were repeated except that each of the compounds of the formula (XI) as indicated in Table 2-1 was used in place of 3-aminopiperidine and that the reaction conditions were changed as indicated in Table 2-1. There were obtained 1-(1-chloro-5-isoquinolinesulfonyl)-3-dimethylaminopiperidine [Compound (99)], 1-(5-isoquinolinesulfonyl)-3-(N-hexyl-N-methylamino)-piperidine [Compound (100)]. The yields and analytical values of these compounds are shown in Table 2-2.

EXAMPLE 3

In 100 ml of ice water was dissolved 10.56 g of 5-isoquinolinesulfonyl chloride hydrochloride, and the pH of the solution was adjusted to 6 with a saturated aqueous sodium hydrogencarbonate solution, followed by extraction with 100 ml of dichloromethane. The dichloromethane layer was added dropwise to a 100 ml of dichloromethane solution containing 8.7 g of N-hexylethanolamine and 6.1 g of triethylamine over 20 minutes while cooling with ice. The mixture was stirred at a temperature of 15° C. to 20° C. for 3 hours, washed with water, and dried with anhydrous magnesium sulfate. Then, thedichloromethane was removed under reduced pressure to obtain an oily residue. The thus obtained oily residue was subjected to purification by silica gel column chromatography (Wacogel C-200, 200 g; solvent: a 5% methanol solution in chloroform) to obtain 5.24 g of N-hexyl-N-(2-hydroxyethyl)-5-isoquinolinesulfonamide.

TABLE 2

| Run No. | 1-Chloro-5-isoquinoline-sulfonyl chloride hydrochloride (g) | Compound (XI) | (g) | Reaction temperature (°C.) | Reaction time (hr) | Obtained compound | Yield | IR spectrum (cm$^{-1}$) | NMR spectrum (CD$_3$OD-DCl) |
|---|---|---|---|---|---|---|---|---|---|
| 2-1 | 1.0 | (piperidine-NMe$_2$) | 1.3 | 15–20 | 3 | (99) | 0.91 g (77%) | 2950, 1340 1160 | 0.8–3.2(12H), 3.3–4.5(3H) 7.4–7.9(1H), 8.0–8.7(4H) |
| 2-2 | 1.0 | (piperidine-N(CH$_3$)(cyclohexyl)) | 2.0 | 15–20 | 3 | (100) | 1.21 g (86%) | 2950, 1340 1160 | 0.8–3.2(19H), 3.3–4.2(4H) 7.4–7.9(1H), 8.0–8.7(4H) |

To 70 ml of pyridine were added 5.24 g of N-hexyl-N-(2-hydroxyethyl)-5-isoquinolinesulfonamide and 3.39 g of p-toluenesulfonyl chloride. The resulting mixture was stirred at 60° C. for 4 hours. Then, the pyridine was removed under reduced pressure to obtain an oily residue. To the residue were added 50 ml of chloroform and 20 ml of an aqueous hydrochloric acid solution having a pH of 2, and the chloroform layer was dried with anhydrous magnesium sulfate. Then, the chloroform was removed under reduced pressure to obtain a residue. The residue thus obtained was subjected to purification by silica gel column chromatography (Wacogel C-200, 100 g; solvent: a 3% methanol solution in chloroform) to obtain 2.60 g of N-hexyl-N-(2-p-toluenesulfonyloxyethyl)-5-isoquinolinesulfonamide.

To 2.34 g of the thus obtained N-hexyl-N-(2-p-toluenesulfonyloxyethyl)-5-isoquinolinesulfonamide was added 40 ml of an ethanol solution containing 4 g of ammonia, and the mixture was heated at 90° C. for 48 hours in a pressure vessel. Then, the solvent was removed under reduced pressure to obtain a residue. The residue thus obtained was subjected to purification by silica gel column chromatography (Wacogel C-200, 100 g; solvent: a 3% methanol solution in chloroform) to obtain 1.34 g of N-hexyl-N-(2-aminoethyl)-5-isoquinolinesulfonamide [Compound (4)]. Compound (4) was analyzed to give the following data.

IR absorption spectrum (cm$^{-1}$): 2920, 1610, 1320, 1150, 1130.

NMR spectrum (CDCl$_3$): 0.6–1.6(13H), 2.7–3.0(2H), 3.1–3.6(4H), 7.5–7.9(1H), 8.1–8.8(4H), 9.4(1H).

Substantially the same procedures as described above were repeated except that in place of N-hexyl-N-(2-hydroxyethyl)-5-isoquinolinesulfonamide, use was made of N-(2-hydroxyethyl)-N-methyl-5-isoquinolinesulfonamide, N-(2-hydroxyethyl)-N-isopropyl-5-isoquinolinesulfonamide, N-(2-hydroxyethyl)-N-butyl-5-isoquinolinesulfonamide, N-(2-hydroxyethyl)-N-octyl-5-isoquinolinesulfonamide, N-(2-hydroxyethyl)-N-benzyl-5-isoquinolinesulfonamide, N-(3-hydroxypropyl)-N-hexyl-5-isoquinolinesulfonamide, N-(4-hydroxybutyl)-N-hexyl-5-isoquinolinesulfonamide, N-(5-hydroxypentyl)-N-hexyl-5-isoquinolinesulfonamide and N-(6-hydroxyhexyl)-N-propyl-5-isoquinolinesulfonamide and that the reaction conditions were changed as indicated in Table 3-1. There were obtained N-(2-aminoethyl)-N-methyl-5-isoquinolinesulfonamide [Compound (1)], N-(2-aminoethyl)-N-isopropyl-5-isoquinolinesulfonamide [Compound (2)], N-(2-aminoethyl)-N-butyl-5-isoquinolinesulfonamide [Compound (3)], N-(2-aminoethyl)-N-octyl-5-isoquinolinesulfonamide [Compound (5)], N-(2-aminoethyl)-N-benzyl- 5-isoquinolinesulfonamide [Compound (6)], N-(3-aminopropyl)-N-hexyl-5-isoquinolinesulfonamide [Compound (7)], N-(4-aminobutyl)-N-hexyl-5-isoquinolinesulfonamide [Compound (8)], N-(5-aminopentyl)-N-hexyl-5-isoquinolinesulfonamide [Compound (9)] and N-(6-aminohexyl)-N-propyl-5-isoquinolinesulfonamide [Compound (10)]. The yields and analytical values of these compounds are shown in Table 3-2.

EXMAPLE 4

In 30 ml of ice water was dissolved 6.0 g of 1-chloro-5-isoquinolinesulfonyl chloride hydrochloride, and the pH of the solution was adjusted to 6 with a saturated aqueous sodium hydrogencarbonate solution, followed by extraction with 50 ml of dichloromethane. The dichloromethane layer was added dropwise to a 50 ml of dichloromethane solution containing 2.1 g of 4-hydroxypiperidine and 2.0 g of triethylamine over 20 minutes while cooling with ice. The mixture was stirred at a temperature of 15° C. to 20° C. for 2 hours, washed with water, and dried with anhydrous magnesium sulfate.

TABLE 3

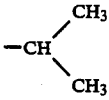

| Run No. | Compound (XIX) R$^2$ | i | (g) | NH$_3$ (g) | Reaction temperature (°C.) | Reaction time (hr) | Obtained compound | Yield | IR spectrum (cm$^{-1}$) | NMR spectrum (CDCl$_3$) |
|---|---|---|---|---|---|---|---|---|---|---|
| 3-1 | —CH$_3$ | 2 | 0.84 | 1.0 | 80 | 24 | (1) | 0.45 g (85%) | 3370, 2930 1615, 1325 1160, 1140 | 2.4(2H), 2.7–3.1(5H) 3.2(2H), 7.5–7.9(1H) 8.1–8.7(4H), 9.4(1H) |
| 3-2 | —CH(CH$_3$)$_2$ | 2 | 0.90 | 1.0 | 80 | 24 | (2) | 0.47 g (80%) | 3410, 2930 1620, 1330 1160, 1140 | 0.85(6H), 2.3–3.3(5H) 3.2(2H), 7.5–7.9(1H) 8.1–8.8(4H), 9.4(1H) |
| 3-3 | —C$_4$H$_9$ | 2 | 0.92 | 1.0 | 90 | 24 | (3) | 0.43 g (70%) | 3350, 2940 1620, 1330 1160, 1140 | 0.6–1.7(9H), 2.8(2H) 3.0–3.6(4H), 7.5–7.8(1H) 8.1–8.7(4H), 9.3(1H) |
| 3-4 | —C$_8$H$_{17}$ | 2 | 1.04 | 1.0 | 90 | 24 | (5) | 0.44 g (60%) | 3350, 2930 1617, 1330 1160, 1140 | 0.7–1.7(15H), 1.8(2H) 2.7–3.1(2H), 3.1–3.7(4H) 7.7–7.9(1H), 8.1–8.8(4H) 9.3(1H) |
| 3-5 | —CH$_2$C$_6$H$_5$ | 2 | 1.00 | 1.0 | 80 | 36 | (6) | 0.44 g (65%) | 3300, 2920 1615, 1320 1150, 1130 | 1.6–2.3(2H), 2.3–2.9(2H) 3.1–3.5(2H), 5.3(2H) 7.2(5H), 7.4–7.8(1H) 8.0–8.7(4H), 9.3(1H) |
| 3-6 | —C$_6$H$_{13}$ | 3 | 1.51 | 1.0 | 80 | 36 | (7) | 0.73 g (70%) | 3340, 2920 1620, 1330 1160, 1140 | 0.6–1.9(15H), 2.5–3.0(2H) 3.1–3.6(4H), 7.5–7.9(1H) 8.0–8.6(4H), 9.3(1H) |
| 3-7 | —C$_6$H$_{13}$ | 4 | 1.55 | 1.0 | 90 | 36 | (8) | 0.81 g (74%) | 3350, 2920 1620, 1330 1160, 1140 | 0.7–1.9(17H), 2.5–3.1(2H) 3.1–3.7(4H), 7.5–7.9(1H) 8.1–8.7(4H), 9.3(1H) |

TABLE 3-continued

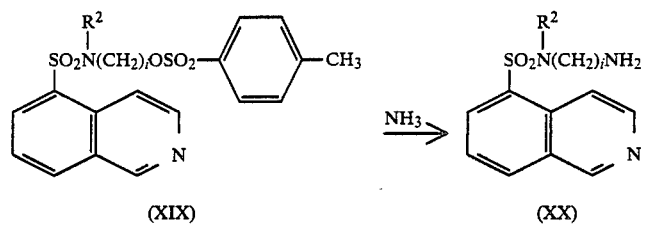

| Run No. | Compound (XIX) R² | i | (g) | NH₃ (g) | Reaction temperature (°C.) | Reaction time (hr) | Obtained compound | Yield | IR spectrum (cm⁻¹) | NMR spectrum (CDCl₃) |
|---|---|---|---|---|---|---|---|---|---|---|
| 3-8 | —C₆H₁₃ | 5 | 1.60 | 1.0 | 90 | 48 | (9) | 0.79 g (70%) | 3340, 2920 1615, 1320 1160, 1145 | 0.7–2.0(19H), 2.4–3.0(2H) 3.1–3.7(4H), 7.5–7.9(1H) 8.1–8.8(4H), 9.3(1H) |
| 3-9 | —C₃H₇ | 6 | 1.51 | 1.0 | 90 | 48 | (10) | 0.65 g (62%) | 3350, 2930 1620, 1330 1150, 1130 | 0.7–2.0(15H), 2.7–3.0(2H) 3.1–3.5(4H), 7.5–7.8(1H) 8.1–8.8(4H), 9.3(1H) |

Then, the dichloromethane was removed under reduced pressure to obtain 6.02 g of 1-(1-chloro-5-isoquinolinesulfonyl)-4-hydroxypiperidine.

To 40 ml of pyridine were added 3.11 g of the thus obtained 1-(1-chloro-5-isoquinolinesulfonyl)-4-hydroxypiperidine and 3.81 g of p-toluenesulfonyl chloride. The resulting mixture was stirred at a temperature of 15° C. to 20° C. for 24 hours. To the reaction mixture was added 100 g of ice water, followed by extraction twice with 100 ml each of dichloromethane. The dichloromethane layer was dried with anhydrous magnesium sulfate and the dichloromethane was removed under reduced pressure to obtain 4.46 g of 1-(1-chloro-5-isoquinolinesulfonyl)-4-p-toluenesulfonyloxypiperidine.

To 50 ml of dichloromethane were added 4.0 g of the thus obtained 1-(1-chloro-5-isoquinolinesulfonyl)-4-p-toluenesulfonyloxypiperidine and 1 ml of a 40% methylamine solution in methanol. The mixture was heated at 70° C. for 6 hours in a sealed vessel. Then, the dichloromethane was removed under reduced pressure to obtain an oily residue. The thus obtained oily residue was subjected to purification by silica gel column chromatography (Wacogel C-200, 100 g; solvent: a 5% methanol solution in chloroform) to obtain 2.28 g of 1-(1-chloro-5-isoquinolinesulfonyl)-4-methylaminopiperidine [Compound (94)] in a yield of 71%. Compound (94) was analyzed to give the following data.

IR absorption spectrum (cm⁻¹): 2950,1340,1160.
NMR spectrum (CD₃OD-DCl): 0.8–2.1(7H), 2.3–3.1(3H), 3.7–4.1(2H), 7.4–7.9(1H), 8.0–8.7(4H).

EXMAPLE 5

To 50 ml of chloroform were added 2.4 g of 1-(1-chloro-5-isoquinolinesulfonyl)-4-p-toluenesulfonyloxypiperidine and 2.1 g of benzylamine. The mixture was heated at 70° C. for 24 hours to obtain 1.43 g of 1-(1-chloro-5-isoquinolinesulfonyl)-4-benzylaminopiperidine [Compound (95)]. Compound (95) was analyzed to give the following data.

IR absorption spectrum (cm⁻¹): 2950,1340,1160.
NMR spectrum (CD₃OD-DCl): 0.8–3.2(7H), 3.7–4.1(4H), 7.4–7.9(6H), 8.0–8.7(4H).

EXAMPLE 6

Substantially the same procedures as in Example 4 were repeated except that 2.1 g of 3-hydroxypiperidine was used in place of 2.1 g of 4-hydroxypiperidine to obtain 4.6 g of 1-(1-chloro-5-isoquinolinesulfonyl)-3-p-toluenesulfonyloxypiperidine.

To 50 ml of dichloromethane were added 4.0 g of the thus obtained 1-(1-chloro-5-isoquinolinesulfonyl)-3-p-toluenesulfonyloxypiperidine and 2 ml of a 40% ethylamine solution in methanol. The mixture was heated at 70° C. for 12 hours in a sealed bottle to obtain 2.1 g of 1-(1-chloro-5-isoquinolinesulfonyl)-3-ethylaminopiperidine [Compound (97)]. Compound (97) was analyzed to give the following data.

IR absorption spectrum (cm⁻¹): 2950, 1340, 1160.
NMR spectrum (CD₃OD-DCl): 0.8–2.1(7H), 2.1–3.2(5H), 3.3–3.8(2H), 7.4–7.9(1H), 8.0–8.7(4H).

EXAMPLE 7

Substantially the same procedures as in Example 4 were repeated except that 5.3 g of 5-isoquinolinesulfonyl chloride hydrochloride was used in place of 6.0 g of 1-chloro-5-isoquinolinesulfonyl chloride hydrochloride to obtain 7.58 g of 1-(5-isoquinolinesulfonyl)-4-p-toluenesulfonyloxypiperidine.

To 50 ml of dichloromethane were added 3.57 g of the thus obtained 1-(5-isoquinolinesulfonyl)-4-p-toluenesulfonyloxypiperidine and 2 ml of a 40% ethylamine solution in methanol. The mixture was heated at 70° C. for 12 hours in a sealed bottle to obtain 2.1 g of 1-(5-isoquinolinesulfonyl)-4-ethylaminopiperidine [Compound (53)]. Compound (53) was analyzed to give the following data.

IR absorption spectrum (cm⁻¹): 2950,1340,1160.
NMR spectrum (CD₃OD-DCl): 0.6–2.1(9H), 2.2–3.1(5H), 3.7–4.1(2H), 7.4–7.9(1H), 8.0–8.7(4H), 9.1–9.3(1H).

Substantially the same procedures as mentioned above were repeated except that 1-(5-isoquinolinesulfonyl)-4-p-toluenesulfonyloxypiperidine was reacted with each of the compounds of formula (XV) as indicated in Table 4-1 in place of ethylamine and that the reaction conditions were changed as indicated in Table 4-1. There were obtained 1-(5-isoquinolinesulfonyl)-4-propylaminopiperidine [Compound (54)], 1-(5-isoquinolinesulfonyl)-4-isopropylaminopiperidine [Compound (55)], 1-(5-isoquinolinesulfonyl)-4-phenethylaminopiperidine [Compound (61)] and 1-(5-isoquinolinesulfonyl)-4-piperidinopiperidine [Compound (62)]. The yields and analytical values of these compounds are shown in Table 4-2.

EXAMPLE 8

In 100 ml of ice water was dissolved 10.6 g of 5-isoquinolinesulfonyl chloride hydrochloride, and the pH of the solution was adjusted to 6 with a saturated aqueous sodium hydrogencarbonate solution, followed by extraction with of 200 ml of dichloromethane. The dichloromethane layer was added dropwise to a 100 ml of dichloromethane solution containing 6.0 g of 3-hydroxypiperidine and 6.0 g of triethylamine over 30 minutes while cooling with ice. The mixture was stirred at a temperature of 15° C. to 20° C. for 3 hours, washed with water, and dried with anhydrous magnesium sulfate. Then, the dichloromethane was removed under reduced pressure to obtain 8.50 g of 1-(5-isoquinolinesulfonyl)-3-hydroxypiperidine.

To 80 ml of pyridine were added 5.84 g of the thus obtained 1-(5-isoquinolinesulfonyl)-3-hydroxypiperidine and 4.2 g of p-toluenesulfonyl chloride. Then, the resulting mixture was stirred at a temperature of 15° C. to 20° C. for 24 hours.

To the reaction mixture was added 100 g of ice water, followed by extraction twice with 100 ml each of dichloromethane. The dichloromethane layer was dried with anhydrous magnesium sulfate and the dichloromethane was removed under reduced pressure to obtain 7.58 g of 1-(5-isoquinolinesulfonyl)-3-p-toluenesulfonyloxypiperidine.

To 50 ml of dichloromethane were added 3.57 g of the thus obtained 1-(5-isoquinolinesulfonyl)-3-p-toluenesulfonyloxypiperidine and 2 ml of a 40% methylamine solution in methanol. The mixture was heated at 70° C. for 12 hours in a sealed vessel to obtain 2.0 g of 1-(5-isoquinolinesulfonyl)-3-methylaminopiperidine [Compound (64)]. Compound (64) was analyzed to give the following data.

IR absorption spectrum (cm$^{-1}$): 2950, 1340, 1160.
NMR spectrum (CD$_3$OD-DCl): 0.8–2.1(7H), 2.1–3.2(3H), 3.3–3.8(2H), 7.4–7.9(1H), 8.0–8.7(4H), 9.1–9.3(1H).

Substantially the same procedures as mentioned above were repeated except that 1-(5-isoquinolinesulfonyl)-3-p-toluenesulfonyloxypiperidine was reacted with each of the compounds of formula (XV) as indicated in Table 5-1 in place of methylamine and that the reaction conditions were changed as indicated in Table 5-1. There were obtained 1-(5-isoquinolinesulfonyl)-3-ethylaminopiperidine [Compound (65)], 1-(5-isoquinolinesulfonyl)-3-propylaminopiperidine [Compound (66)], 1-(5-isoquinolinesulfonyl)-3-isopropylaminopiperidine [Compound (67)], 1-(5-isoquinolinesulfonyl)-3-phenethylaminopiperidine [Compound (70)] and 1-(5-isoquinolinesulfonyl)-3-hexylaminopiperidine [Compound (71)]. The yields and analytical values of these compounds are shown in Table 5-2.

TABLE 4

| Run No. | Compound (XXI) (g) | Compound (XV) | (g) | Reaction medium | (ml) | Reaction temperature (°C.) | Reaction time (hr) | Obtained compound (XXII) | Yield | IR spectrum (cm$^{-1}$) | NMR spectrum (CD$_3$OD-DCl) |
|---|---|---|---|---|---|---|---|---|---|---|---|
| 4-1 | 2.23 | H$_2$N(CH$_2$)$_2$CH$_3$ | 0.6 | CHCl$_3$ C$_2$H$_5$OH | 30 2 | 80 | 24 | (54) | 1.07 g (86%) | 2950, 1340 1160 | 0.6–2.1(9H), 2.2–4.1(7H) 7.4–7.9(1H), 8.0–8.7(4H) 9.3(1H) |
| 4-2 | 2.23 | H$_2$NCH(CH$_3$)$_2$ | 0.6 | CHCl$_3$ C$_2$H$_5$OH | 30 2 | 80 | 24 | (55) | 0.88 g (70%) | 2950, 1340 1160 | 0.6–2.1(10H), 2.2–4.1(6H) 7.4–7.9(1H), 8.0–8.7(4H) 9.3 (1H) |
| 4-3 | 2.23 | H$_2$N(CH$_2$)$_2$C$_6$H$_5$ | 0.8 | CHCl$_3$ | 30 | 80 | 24 | (61) | 1.23 g (79%) | 2950, 1340 1160 | 0.8–3.2(6H), 3.3–4.2(7H) 7.4–7.9(6H), 8.0–8.7(4H) 9.3(1H) |
| 4-4 | 2.23 | HN(cyclohexyl) | 0.8 | CHCl$_3$ | 30 | 80 | 24 | (62) | 0.84 g (61%) | 2950, 1340 1160 | 0.8–3.2(15H), 3.7–4.1(4H) 7.4–7.9(1H), 8.0–8.7(4H) 9.3(1H) |

EXAMPLE 9

To 50 ml of a dried dichloromethane solution containing 1.27 g of oxalyl chloride was added dropwise at −50° C. 10 ml of a dichloromethane solution containing 0.78 g of dimethylsulfoxide. The mixture was allowed to stand for 2 minutes. To the mixture was dropwise added over a period of 5 minutes, while maintaining the temperature at −55° C., 20 ml of a dried dichloromethane solution containing 3.11 g of 1-(1-chloro-5-isoquinolinesulfonyl)-3-hydroxypiperidine as obtained in Example 6, followed by stirring at that temperature for 20 minutes. To the resulting mixture was added 0.70 ml of triethylamine, and the mixture was stirred for 5 munutes.

dine as obtained in Example 4 was reacted, in substantially the same manner as in Example 9, with oxalyl chloride, dimethylsulfoxide and triethylamine to obtain

TABLE 5

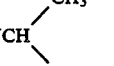

| Run No. | Compound (XXIII) (g) | Compound (XV) | (g) | Reaction medium | (ml) | Reaction temperature (°C.) | Reaction time (hr) | Obtained compound (XXIV) | Yield | IR spectrum (cm⁻¹) | NMR spectrum (CD₃OD—DCl) |
|---|---|---|---|---|---|---|---|---|---|---|---|
| 5-1 | 2.23 | H₂NC₂H₅ | 0.6 | CHCl₃ C₂H₅OH | 30 2 | 70 | 12 | (65) | 0.80 g (68%) | 2950, 1340 1160 | 0.8–2.0(7H), 7.4–7.9(1H) 2.1–3.2(5H), 8.0–8.7(4H) 3.3–3.8(2H), 9.1–9.3(1H) |
| 5-2 | 2.23 | H₂N(CH₂)₂CH₃ | 0.6 | CHCl₃ C₂H₅OH | 30 2 | 70 | 12 | (66) | 0.71 g (57%) | 2950, 1340 1160 | 0.6–2.0(9H), 7.4–7.9(1H) 2.1–3.2(5H), 8.0–8.7(4H) 3.3–3.8(2H), 9.1–9.3(1H) |
| 5-3 | 2.23 | H₂NCH(CH₃)₂ | 0.6 | CHCl₃ C₂H₅OH | 30 2 | 70 | 12 | (67) | 0.79 g (63%) | 2950, 1340 1160 | 0.6–2.0(9H), 7.4–7.9(1H) 2.1–3.2(5H), 8.0–8.7(4H) 3.3–3.8(2H), 9.1–9.3(1H) |
| 5-4 | 2.23 | H₂N(CH₂)₂C₆H₅ | 1.0 | CHCl₃ | 30 | 80 | 18 | (70) | 1.26 g (81%) | 2950, 1340 1160 | 0.8–3.2(9H), 3.3–4.5(4H) 7.4–7.9(6H), 8.0–8.7(4H) 9.3(1H) |
| 5-5 | 2.23 | H₂NC₆H₁₃ | 1.0 | CHCl₃ | 30 | 80 | 18 | (71) | 1.11 g (76%) | 2950, 1340 1160 | 0.8–1.5(15H), 1.8–4.5(7H) 7.4–7.9(1H), 8.0–8.8(4H) 9.3(1H) |

Then, the temperature of the mixture was raised to 15° to 20° C. The mixture was washed twice with 100 ml each of water and dried with anhydrous sodium sulfate. Then, the dichloromethane was removed under reduced pressure to obtain a residue. The residue thus obtained was subjected to purification by silica gel column chromatography (Wacogel C-200, 100 g; solvent: chloroform) to obtain 2.75 g of 1-(1-chloro-5-isoquinolinesulfonyl)-3-piperidone.

To 50 ml of methanol were added 2.47 g of the thus obtained 1-(1-chloro-5-isoquinolinesulfonyl)-3-piperidone, 1.11 g of n-hexylamine hydrochloride and 0.50 g of sodium cyanoborohydride, followed by stirring at 20° C. for 15 hours. The methanol was removed under reduced pressure, and 50 ml of chloroform was added to the resultant product. Then, the mixture was washed twice with 50 ml each of water and then washed once with 50 ml of a 50% aqueous sodium hydrogencarbonate solution, and dried with anhydrous sodium sulfate. The solvent was removed under reduced pressure to obtain a residue. The residue thus obtained was subjected to purification by silica gel column chromatography (Wacogel C-200, 100 g; solvent: chloroform) to obtain 2.54 g of 1-(1-chloro-5-isoquinolinesulfonyl)-3-hexylaminopiperidine [Compound (98)]. Compound (98) was analyzed to give the following data.

IR absorption spectrum (cm⁻¹): 2950,1340,1160.

NMR spectrum (CD₃OD-DCl): 0.8–2.0(15H), 2.1–3.2(3H), 3.3–3.8(2H), 7.4–7.9(1H), 8.0–8.7(4H).

EXAMPLE 10

In place of 3.11 g of 1-(1-chloro-5-isoquinolinesulfonyl)-3-hydroxypiperidine used in Example 9, 3.11 g of 1-(1-chloro-5-isoquinolinesulfonyl)-4-hydroxypiperidine as obtained in Example 4 was reacted, in substantially the same manner as in Example 9, with oxalyl chloride, dimethylsulfoxide and triethylamine to obtain 2.78 g of 1-(1-chloro-5-isoquinolinesulfonyl)-4-piperidone.

To 50 ml of methanol were added 2.60 g of 1-(1-chloro-5-isoquinolinesulfonyl)-4-piperidone, 0.60 g of methylamine hydrochloride and 0.56 g of sodium cyanoborohydride. The reaction was effected in substantially the same manner as in Example 9 to obtain 1.68 g of 1-(1-chloro-5-isoquinolinesulfonyl)-4-methylaminopiperidine [Compound (94)]. Compound (94) was analyzed to give the following data.

IR absorption spectrum (cm⁻¹): 2950,1340,1160.

NMR spectrum (CD₃OD-DCl): 0.8–2.1(7H), 2.3–3.1(3H), 3.7–4.1(2H), 7.4–7.9(1H), 8.0–8.7(4H).

EXAMPLE 11

Substantially the same procedures as in Example 4 were repeated except that 1.8 g of 3-hydroxypyrrolidine was used in place of 2.1 g of 4-hydroxypiperidine to obtain 1-(1-chloro-5-isoquinolinesulfonyl)-3-hydroxypyrrolidine. Then, in substantially the same manner as in Example 10, 2.5 g of the thus obtained 1-(1-chloro-5-isoquinolinesulfonyl)-3-hydroxypyrrolidine was reacted in dichloromethane with 1.08 g of oxalyl chloride, 0.67 g of dimethylsulfoxide and 0.60 g of triethylamine to obtain 1-(1-chloro-5-isoquinolinesulfonyl)-3-pyrrolidone.

Then, in place of 2.60 g of 1-(1-chloro-5-isoquinolinesulfonyl)-4-piperidone in Example 10, 2.48 g of the thus obtained 1-(1-chloro-5-isoquinolinesulfonyl)-3-pyrrolidone was reacted with methylamine hydrochloride in substantially the same manner as in Example 10 to obtain 2.08 g of 1-(1-chloro-5-isoquinolinesulfonyl)-3-methylaminopyrrolidine [Compound (102)]. Compound (102) was analyzed to give the following data.

IR absorption spectrum (cm$^{-1}$): 2950,1340,1160.
NMR spectrum (CD$_3$OD-DCl): 0.8–2.0(2H), 2.1–3.2(6H), 3.3–4.0(2H), 7.4–7.9(1H), 8.0–8.7(4H).

EXAMPLE 12

Substantially the same procedures as in Example 11 were repeated except that 6.16 g of ammonium acetate was used in place of 0.60 g of methylamine hydrochloride, thereby to obtain 1.89 g of 1-(1-chloro-5-isoquinolinesulfonyl)-3-aminopyrrolidine [Compound (101)]. Compound (101) was analyzed to give the following data.

IR absorption spectrum (cm$^{-1}$): 2950,1340,1160.
NMR spectrum (CDCl$_3$-DCl): 0.8–2.0(2H), 2.1–3.2(3H), 3.3–4.0(2H), 7.4–7.9(1H), 8.0–8.7(4H).

EXAMPLE 13

To 100 ml of a dried dichloromethane solution containing 2.67 g of oxalyl chloride was added dropwise at −50° C. 20 ml of a dichloromethane solution containing 1.64 g of dimethylsulfoxide. The mixture was allowed to stand for 5 minutes. To the mixture was added dropwise over a period of 10 minutes, while maintaining the temperature at −55° C., 40 ml of a dried dichloromethane solution containing 5.84 g of 1-(5-isoquinolinesulfonyl)-4-hydroxypiperidine as obtained in Example 7, followed by stirring at that temperature for 20 minutes. To the resulting mixture was added 1.4 ml of triethylamine, and the mixture was stirred for 5 minutes. Then, the temperature of the mixture was raised to 15° C. The mixture was washed twice with 100 ml each of water and dried with anhydrous sodium sulfate. Then, the dichloromethane was removed under reduced pressure to obtain a residue. The residue thus obtained was subjected to purification by silica gel column chromatography (Wacogel C-200, 150 g; solvent: chloroform) to obtain 5.16 g of 1-(5-isoquinolinesulfonyl)-4-piperidone.

To 50 ml of methanol were added 2.9 g of the thus obtained 1-(5-isoquinolinesulfonyl)-4-piperidone, 2.31 g of ammonium acetate and 0.63 g of sodium cyanoborohydride, followed by stirring at 20° C. for 24 hours. The methanol was removed under reduced pressure, and 100 ml of chloroform was added to the resultant product. Then, the mixture was washed twice with 50 ml each of water, washed once with 50 ml of a 50% aqueous sodium hydrogencarbonate solution, and dried with anhydrous sodium sulfate. The solvent was removed under reduced pressure to obtain a residue. The residue thus obtained was subjected to purification by silica gel column chromatography (Wacogel C-200, 150 g; solvent: chloroform) to obtain 2.39 g of 1-(5-isoquinolinesulfonyl)-4-aminopiperidine [Compound (51)]. Compound (51) was analyzed to give the following data.

IR absorption spectrum (cm$^{-1}$): 2950,1340,1160.
NMR spectrum (CD$_3$OD-DCl): 1.3–1.7(6H), 2.9–3.3(3H), 7.4–7.9(1H), 8.0–8.7(4H), 9.1–9.3(1H).

Substantially the same procedures as mentioned above were repeated except that 1-(5-isoquinolinesulfonyl)-4-piperidone was reacted with each of the compounds of formula (XV) as indicated in Table 6-1 in place of ammonium acetate and that the reaction conditions were changed as indicated in Table 6-1. There were obtained 1-(5-isoquinolinesulfonyl)-4-methylaminopiperidine [Compound (52)], 1-(5-isoquinolinesulfonyl)-4-butylaminopiperidine [Compound (56)], 1-(5-isoquinolinesulfonyl)-4-hexylaminopiperidine [Compound (57)]and 1-(5-isoquinolinesulfonyl)-4-benzylaminopiperidine [Compound (60)].

TABLE 6

| Run No. | Compound (XXV) (g) | Compound (XV).HCl (g) | NaCNBH$_3$ (g) | Reaction temperature (°C.) | Reaction time (hr) | Obtained compound (XXVI) | Yield | IR spectrum (cm$^{-1}$) | NMR spectrum (CD$_3$OD—DCl) |
|---|---|---|---|---|---|---|---|---|---|
| 6-1 | 1.45 | H$_2$NCH$_3$.HCl 0.68 | 0.32 | 20 | 24 | (52) | 1.13 g (74%) | 2950, 1340 1160 | 0.8–2.1(7H), 2.3–3.1(3H) 3.7–4.1(2H), 7.4–7.9(1H) 8.0–8.7(4H), 9.3(1H) |
| 6-2 | 1.45 | H$_2$NC$_4$H$_9$.HCl 1.1 | 0.32 | 20 | 24 | (56) | 2.51 g (77%) | 2950, 1340 1160 | 0.6–2.1(11H), 2.2–3.2(5H) 3.7–4.1(2H), 7.4–7.9(1H) 8.0–8.7(4H), 9.3(1H) |
| 6-3 | 0.87 | H$_2$NC$_6$H$_{13}$.HCl 0.83 | 0.20 | 20 | 18 | (57) | 0.96 g (85%) | 2950, 1340 1160 | 0.6–2.1(15H), 2.2–3.2(5H) 3.7–4.1(2H), 7.4–7.9(1H) 8.0–8.7(4H), 9.3(1H) |
| 6-4 | 0.87 | H$_2$NCH$_2$C$_6$H$_5$.HCl 0.86 | 0.20 | 20 | 18 | (60) | 0.72 g (63%) | 2950, 1340 1160 | 0.8–3.2(7H), 3.7–4.2(4H) 7.4–7.9(6H), 8.0–8.7(4H) 9.3(1H) |

The yields and analytical values of these compounds are shown in Table 6-2.

EXAMPLE 14

Substantially the same procedures as in Example 13 were repeated except that 5.84 g to 1-(5-isoquinolinesulfonyl)-3-hydroxypiperidine was used in place of 5.84 g of 1-(5-isoquinolinesulfonyl)-4-hydroxypiperidine and that 2.9 g of the thus obtained 1-(5-isoquinolinesulfonyl)-3-piperidone was reacted in methanol with 2.31 g of ammonium acetate and 0.63 g of sodium cyanoborohydride at 20° C. for 24 hours. There was obtained 2.37 g of 1-(5-isoquinolinesulfonyl)-3-aminopiperidine [Compound(63)]. Compound (63) was analyzed to give the following data.

IR absorption spectrum (cm$^{-1}$): 2950, 1340,1160.

NMR spectrum (CD$_3$OD-DCl): 0.8–2.0(4H), 2.1–3.2(3H), 3.3–3.8(2H), 7.4–7.9(1H), 8.0–8.7(4H), 9.1–9.3(1H).

Substantially the same procedures as mentioned above were repeated except that 1-(5-isoquinolinesulfonyl)-3-piperidone was reacteed with each of the compounds of formula (XV) as indicated in Table 7-1 in place of ammonium acetate and that the reaction conditons were changed as indicated in Table 7-1.

NMR spectrum (CD$_3$OD-DCl): 0.8–2.0(2H), 2.1–3.2(5H), 3.3–4.0(2H), 7.4–7.9(1H), 8.0–8.7(4H), 9.1–9.3(1H).

Likewise, 1-(5-isoquinolinesulfonyl)-3-aminopyrrolidine [Compound (78)] was obtained from 1-(5-isoquinolinesulfonyl)-3-pyrrolidone. Compound (78) was analyzed to give the following data.

IR absorption spectrum (cm$^{-1}$): 2950,1340,1160.

NMR spectrum (CD$_3$OD-DCl): 0.8–2.0(2H), 2.1–3.2(3H), 3.3–4.0(2H), 7.4–7.9(1H), 8.0–8.7(4H), 9.1–9.3(1H).

EXAMPLE 16

TABLE 7

| Run No. | Compound (XXVII) (g) | Compound (XV).HCl (g) | NaCNBH$_3$ (g) | Reaction temperature (°C.) | Reaction time (hr) | Obtained compound (XXVIII) | Yield | IR spectrum (cm$^{-1}$) | NMR spectrum (CD$_3$OD—DCl) |
|---|---|---|---|---|---|---|---|---|---|
| 7-1 | 1.45 | H$_2$NCH$_2$C$_6$H$_5$.HCl 1.44 | 0.32 | 20 | 15 | (69) | 1.37 g (72%) | 2950, 1340 1160 | 0.8–2.0(4H), 2.1–3.2(3H) 3.3–3.8(4H), 7.4–7.9(6H) 8.0–8.7(4H), 9.3(1H) |
| 7-2 | 1.45 | H$_2$NCH$_2$CH$_2$C$_6$H$_5$.HCl 1.58 | 0.32 | 20 | 15 | (70) | 1.60 g (81%) | 2950, 1340 1160 | 0.8–3.2(9H), 3.3–3.8(4H) 7.4–7.9(6H), 8.0–8.7(4H) 9.3(1H) |
| 7-3 | 1.45 | HN⟨⟩.HCl 1.22 | 0.32 | 20 | 18 | (72) | 1.26 g (70%) | 2950, 1340 1160 | 0.6–2.0(12H), 2.1–3.8(7H) 7.4–7.9(1H), 8.0–8.7(4H) 9.3(1H) |

There were obtained 1-(5-isoquinolinesulfonyl)-3-benzylaminopiperidine [Compound (69)], 1-(5-isoquinolinesulfonyl)-3-phenethylaminopiperidine [Compound (70)] and 1-(5-isoquinolinesulfonyl)-3-piperidinopiperidine [Compound (72)]. The yields and analytical values of these compounds are shown in Table 7-2.

EXAMPLE 15

Substantially the same procedures as in Example 1 were repeated except that 2.64 g of 1-isoquinolinesulfonyl chloride hydrochloride was used in place of 6.0 g of 1-chloro-5-isoquinolinesulfonyl chloride hydrochloride and that 2.22 g of the thus obtained 1-(5-isoquinolinesulfonyl)-3-hydroxypyrrolidine was reacted in dichloromethane with 1.08 g of oxalyl chloride and 0.67 g of dimethylsulfoxide. There was obtained 1-(5-isoquinolinesulfonyl)-3-pyrrolidone.

Then, in place of 2.48 g of 1-(1-chloro-5-isoquinolinesulfonyl)-3-pyrrolidone in Example 11, 2.21 g of the thus obtained 1-(5-isoquinolinesulfonyl)-3-pyrrolidone was reacted with methylamine hydrochloride in substantially the same manner as in Example 11 to obtain 1.72 g of 1-(5-isoquinolinesulfonyl)-3-methylaminopyrrolidine [Compound (76)]. Compound (76) was analyzed to give the following data.

IR absorption spectrum (cm$^{-1}$): 2950,1340,1160.

In substantially the same manner as in Example 11, 2.64 g of 5-isoquinolinesulfonyl chloride hydrochloride was reacted with 2.0 g of 3-hydroxy-5-methylpyrrolidine to obtain 1-(5-isoquinolinesulfonyl)-3-hydroxy-5-methylpyrrolidine.

Then, in substantially the same manner as in Example 9, 2.34 g of the thus obtained 1-(5-isoquinolinesulfonyl)-3-hydroxy-5-methylpyrrolidine was reacted in dichloromethane with 1.08 g of oxalyl chloride, 0.67 g of dimethylsulfoxide and 0.60 g of triethylamine to obtain 1-(5-isoquinolinesulfonyl)-5-methyl-3-pyrrolidone.

To 30 ml of methanol were added 1.45 g of the thus obtained 1-(5-isoquinolinesulfonyl)-5-methyl-3-pyrrolidone, 0.39 g of ammonium acetate and 0.32 g of sodium cyanoborohydride, followed by stirring at 20° C. for 24 hours. The methanol was removed under reduced pressure, and 100 ml of chloroform was added to the resultant product. Then, the mixture was washed twice with 50 ml each of water, washed once with 50 ml of a 50% aqueous sodium hydrogencarbonate solution, and dried with anhydrous sodium sulfate. The solvent was removed under reduced pressure to obtain a residue. The residue thus obtained was subjected to purification by silica gel column chromatography (Wacogel C200, 50 g; solvent: chloroform) to obtain 0.96 g of 1-(5-isoquinolinesulfonyl)-3-amino-5-methylpyrrolidine

[Compound (77)]. Compound (77) was analyzed to give the following data.

IR absorption spectrum (cm$^{-1}$): 2950,1340,1160.

NMR spectrum (CD$_3$OD-DCl: 0.8–3.0(6H), 3.3–4.3(3H), 7.4–7.9(1H), 8.0–8.7(4H), 9.1–9.3(1H).

EXAMPLE 17

In 100 ml of ice water was dissolved 8.8 g of 5-isoquinolinesulfonyl chloride hydrochloride, and the pH of the solution was adjusted to 6 with a saturated aqueous sodium hydrogencarbonate solution, followed by extraction with 100 ml of dichloromethane. The dichloromethane layer was added dropwise to a 100mml of dichloromethane solution containing 5.30 g of N-hexyl-2-hydroxypropylamine and 4.0 g of triethylamine over a period of 20 minutes while cooling with ice. The mixture was stirred at a temperature of 15° C. to 20° C. for 2 hours, washed with water, and dried with anhydrous magnesium sulfate. Then, the dichloromethane was removed under reduced pressure to obtain an oily residue. The thus obtained oily residue was subjected to purification by silica gel column chromatography (Wacogel C-200, 200 g; solvent: a 2% methanol solution in chloroform) to obtain 9.02 g of N-hexyl-N-(2-hydroxypropyl)-5-isoquinolinesulfonamide.

To 60 ml of a dried dichloromethane solution containing 2.4 ml of oxalyl chloride was added dropwise at −50° C. 12 ml of a dichloromethane solution containing 4.08 ml of dimethylsulfoxide. To the mixture was added dropwise over a period of 20 minutes, while maintaining the temperature at −55° C., 4 ml of a dried dichloromethane solution containing 8.34 g of N-hexyl-N-(2-hydroxypropyl)-5-isoquinolinesulfonamide, followed by stirring at −50° C. to −60° C. for 15 minutes. To the resulting mixture was added 16.8 ml of triethylamine, and the temperature of the mixture was elevated to 15° to 20° C. over a period of 1.5 hours. To the resulting reaction mixture was added 100 ml of water, and the pH was adjusted to 5 with 1N hydrochloric acid solution. The dichloromethane layer was washed with 50 ml of a saturated aqueous sodium chloride solution and dried with anhydrous magnesium sulfate. Then, the dichloromethane was removed under reduced pressure to obtain a residue. The residue thus obtained was subjected to purification by silica gel column chromatography (Wacogel C-200, 200 g; solvent: a 2% methanol solution in chloroform) to obtain 7.17 g of N-acetonyl-N-hexyl-5-isoquinolinesulfonamide.

To 75 ml of an anhydrous methanol solution containing 5.89 g of the thus obtained N-acetonyl-N-hexyl-5-isoquinolinesulfonamide were added 13.03 g of ammonium acetate and 0.75 g of sodium cyanoborohydride, followed by stirring at 15° to 20° C. for 19 hours. Then, the methanol was removed at 30° C. under reduced pressure. To the resultant reaction product were added 50 ml of chloroform and 50 ml of 1N sodium hydroxide solution. The chloroform layer was dried with anhydrous magnesium sulfate, and the chloroform was removed under reduced pressure to obtain a residue. The residue thus obtained was subjected to purification by silica gel column chromatography (Wacogel C-200, 100 g; solvent: chloroform) to obtain 2.75 g of N-(2-aminopropyl)-N-hexyl-5-isoquinolinesulfonamide [Compound (11)]. Compound (11) was analyzed to give the following data.

IR absorption spectrum (cm$^{-1}$): 2920, 1610, 1310, 1140.

NMR spectrum (CDCl$_3$): 0.5–1.6(16H), 2.8–3.4(5H), 3.3–3.8(2H), 7.5–7.8(1H), 8.1–8.8(4H), 9.4(1H).

Mass spectrum (m/e): 349.

Likewise, in place of N-hexyl-2-hydroxypropylamine, use was made of each of N-hexyl-2-hydroxybutylamine, N-hexyl-2-hydroxyoctylamine, 2-hydroxy-N-propyldecylamine, N-hexyl-2-hydroxydecylamine and N-butyl-2-hydroxy-1-methylpropylamine to obtain the corresponding compounds of the formula (XIII). Then, each of the compounds thus obtained was reacted with oxalyl chloride, dimethylsulfoxide and triethylamine under the same conditions as mentioned above to obtain compounds of the formula (XVI), i.e., N-hexyl-N-(2-oxobutyl)-5-isoquinolinesulfonamide, N-hexyl-N-(2-oxooctyl)-5-isoquinolinesulfonamide, N-(2-oxodecyl)-N-propyl-5-isoquinolinesulfonamide, N-hexyl-N-(2-oxodecyl)-5-isoquinolinesulfonamide and N-butyl-N-(1-methyl-2-oxopropyl)-5-isoquinolinesulfonamide. Each of the compounds thus obtained was reacted with ammonium acetate in substantially the same manner as mentioned above except that the reaction conditions were changed as indicated in Table 8-1. There were obtained N-(2-aminobutyl)-N-hexyl-5-isoquinolinesulfonamide [Compound (12)], N-(2-aminooctyl)-N-hexyl-5-isoquinolinesulfonamide [Compound (13)], N-(2-aminodecyl)-N-propyl-5-isoquinolinesulfonamide [Compound (14)], N-(2-aminodecyl)-N-hexyl-5-isoquinolinesulfonamide [Compound (15)] and N-(2-amino-1-methylpropyl)-N-butyl-5-isoquinolinesulfonamide [Compound (16)]. The yields and analytical values of these compounds are shown in Table 8-2.

EXAMPLE 18

In 30 ml of pyridine was dissolved 2.67 g of N-hexyl-N-(1-hydroxymethylpentyl)-5-isoquinolinesulfonamide, and 1.56 g of p-toluenesulfonyl chloride was added to the solution. The mixture thus obtained was heated at 60° C. for 17 hours, and then the pyridine was removed under reduced pressure to obtain a residue.

TABLE 8

$$\text{(XXIX)} \xrightarrow[\text{NaCNBH}_3]{\text{NH}_4\text{OAc}} \text{(XXX)}$$

where (XXIX) is the isoquinoline derivative with SO$_2$N(R$^2$)—A—C(R$^3$)=O and (XXX) is the isoquinoline derivative with SO$_2$N(R$^2$)—A—CH(R$^3$)NH$_2$.

| Run No. | Compound (XXIX) R$^2$ | A | R$^3$ | (g) | NH$_4$OAc (g) | NaCNBH$_3$ (mg) | Reaction temperature (°C.) | Reaction time (hr) | Obtained compound (XXX) | Yield | Mass spectrum (m/e) | IR spectrum (cm$^{-1}$) | NMR spectrum (CDCl$_3$) |
|---|---|---|---|---|---|---|---|---|---|---|---|---|---|
| 8-1 | C$_6$H$_{13}$ | —CH$_2$— | C$_2$H$_5$ | 0.36 | 0.40 | 70 | 20–25 | 12 | (12) | 0.15 g (40%) | 363 | 2910, 1615 1310, 1160 1135 | 0.7–2.2(18H) 3.4–4.0(5H) 7.7–8.2(1H) 8.3–8.9(4H) 9.4(1H) |
| 8-2 | " | " | C$_6$H$_{13}$ | 0.42 | 0.40 | 70 | 20–25 | 12 | (13) | 0.08 g (20%) | 419 | 2900, 1605 1350, 1160 1140 | 0.7–1.8(26H) 2.7–3.6(5H) 7.6–8.0(1H) 8.1–8.9(4H) 9.4(1H) |
| 8-3 | C$_3$H$_7$ | " | C$_8$H$_{17}$ | 0.40 | 0.40 | 70 | 20–25 | 15 | (14) | 0.07 g (18%) | 405 | 2920, 1610 1340, 1160 1140 | 0.6–2.2(24H) 3.1–3.9(5H) 7.6–8.1(1H) 8.4–9.0(4H) 9.4(1H) |
| 8-4 | C$_6$H$_{13}$ | " | " | 0.45 | 0.40 | 70 | 20–25 | 18 | (15) | 0.07 g (15%) | 447 | 2920, 1620 1330, 1140 | 0.6–2.2(30H) 3.0–3.9(5H) 7.5–8.2(1H) 8.4–9.0(4H) 9.5(1H) |
| 8-5 | C$_4$H$_9$ | —CH— \| CH$_2$ | CH$_3$ | 0.33 | 0.40 | 70 | 20–25 | 18 | (16) | 0.12 g (36%) | 335 | 2920, 1615 1350, 1160 1140 | 0.7–1.9(15H) 3.0–4.0(4H) 7.7–8.2(1H) 8.4–9.0(4H) 9.4(1H) |

To the residue were added 50 ml of chloroform and 50 ml of a hydrochloric acid solution having a pH of 3. The chloroform layer was dried with anhydrous magnesium sulfate and then the chloroform was removed under reduced pressure to obtain a residue. The residue thus obtained was subjected to purification by silica gel column chromatography (Wacogel C-200, solvent: chloroform) to obtain 2.37 g of N-hexyl-N-(1-p-toluenesulfonyloxymethylpentyl)-5-isoquinolinesulfonamide.

To 2.37 g of the thus obtained N-hexyl-N-(1-p-toluenesulfonyloxymethylpentyl)-5-isoquinolinesulfonamide was added 40 ml of an ethanol solution containing 4 g of ammonia, and the mixture was heated in a pressure vessel at 100° C. for 13 hours. Then, the solvent was removed under reduced pressure to obtain a residue. The residue thus obtained was subjected to purification by silica gel column chromatography (Wacogel C-200, solvent: a 5% methanol solution in chloroform) to obtain 0.70 g of N-(1-aminomethylpentyl)-N-hexyl-5-isoquinolinesulfonamide [Compound (19)]. Compound (19) was analyzed to give the following data.

IR absorption spectrum (cm$^{-1}$): 2925, 1610, 1310, 1140.

NMR spectrum (CDCl$_3$): 0.6–1.7(22H), 3.0–3.8(5H), 7.5–7.8(1H), 8.0–8.8(4H), 9.4(1H).

Mass spectrum (m/e): 391.

Likewise, there were obtained, as compounds represented by the formula (XIV), N-(2-p-toluenesulfonyloxy-1-methylethyl)-N-ethyl-5-isoquinolinesulfonamide, N-(1-p-toluenesulfonyloxymethyl-2-methylpropyl)-N-propyl-5-isoquinolinesulfonamide, N-(3-p-toluenesulfonyloxy-2-methylpropyl)-N-propyl-5-isoquinolinesulfonamide, N-(4-p-toluenesulfonyloxy-1-methylbutyl)-N-hexyl-5-isoquinolinesulfonamide, N-(5-p-toluenesulfonyloxymethylhexyl)-N-ethyl-5-isoquinolinesulfonamide, N-(4-p-toluenesulfonyloxy-3-methylbutyl)-N-hexyl-5-isoquinolinesulfonamide and N-(4-p-toluenesulfonyloxy-1-propylbutyl)-N-hexyl-5-isoquinolinesulfonamide.

Each of the thus obtained compounds of formula (XIV) was reacted with ammonia in substantially the same manner as mentioned above except that the reaction conditions were changed as indicated in Table 9-1. There were obtained N-(2-amino-1-methylethyl)-N-ethyl-5-isoquinolinesulfonamide [Compound (17)], N-(1-aminometyl-2-methylpropyl)-N-propyl-5-isoquinolinesulfonamide [Compound (18)], N-(3-amino-2-methylpropyl)-N-propyl-5-isoquinolinesulfonamide [Compound (20)], N-(4-amino-1-methylbutyl)-N-hexyl-5-isoquinolinesulfonamide [Compound (21)], N-(5-aminomethylhexyl)-N-ethyl-5-isoquinolinesulfonamide [Compound (22)], N-(4-amino-3-methylbutyl)-N-hexyl-5-isoquinolinesulfonamide [Compound (23)] and N-(4-amino-1-propylbutyl)-N-hexyl-5-isoquinolinesulfonamide [Compound (24)]. The yields and analytical values of these compounds are shown in Table 9-2.

EXAMPLE 19

To 5.77 g of N-ethyl-N-(2-hydroxyethyl)-5-isoquinolinesulfonamide were added 100 ml of pyridine and 4.0 g of p-toluenesulfonyl chloride. The mixture thus obtained was heated at 80° C. for 48 hours, and then the pyridine was removed under reduced pressure to obtain a residue. To the residue was added 100 ml of dichloromethane, and the resultant mixture was washed thrice with a hydrochloric acid solution having a pH of 5 and dried with anhydrous magnesium sulfate. Then, the dichloromethane was removed under reduced pressure to obtain a residue. The residue was subjected to purification by silica gel column chromatography (Wacogel C-200, solvent: a 5% methanol solution in chloroform) to obtain 3.96 g of N-ethyl-N-(2-p-toluenesulfonyloxyethyl)-5-isoquinolinesulfonamide.

hours, and then the dioxane was removed under reduced pressure to obtain a crude product. Then, 60 ml of dichloromethane was added to the crude product, and the mixture thus obtained was washed with 30 ml of water and dried with anhydrous magnesium sulfate. The dichloromethane was removed under reduced pressure to obtain a residue. The residue thus obtained was subjected to purification by silica gel column chromatography (Wacogel C-200, solvent: a 5% methanol solution in chloroform) to obtain 2.50 g of N-ethyl-N-(2-hexylaminoethyl)-5-isoquinolinesulfonamide [Compound (28)]. Compound (28) was analyzed to give the

TABLE 9

Isoquinoline-SO$_2$N(R$^2$)—A—CH$_2$OSO$_2$—C$_6$H$_4$—CH$_3$ (XXXI) $\xrightarrow{NH_3/EtOH}$ Isoquinoline-SO$_2$N(R$^2$)—A—CH$_2$NH$_2$ (XXXII)

| Run No. | Compound (XXXI) R$^2$ | A | (g) | NH$_3$ (g) | EtOH (ml) | Reaction temperature (°C.) | Reaction time (hr) | Obtained compound (XXXII) | Yield | Mass spectrum (m/e) | IR spectrum (cm$^{-1}$) | NMR spectrum (CDCl$_3$) |
|---|---|---|---|---|---|---|---|---|---|---|---|---|
| 9-1 | C$_2$H$_5$ | —CH(CH$_3$)— | 1.34 | 2.0 | 20 | 100 | 13 | (17) | 0.35 g (40%) | 293 | 2920, 1610 1310, 1140 1125 | 1.05(d)(3H) 1.2(t)(3H) 2.5–3.8(7H) 7.7–8.0(1H) 8.2–8.9(4H) 9.5(1H) |
| 9-2 | C$_3$H$_7$ | —CH(CH(CH$_3$)$_2$)— | 1.47 | 2.0 | 20 | 100 | 13 | (18) | 0.30 g (30%) | 335 | 2925, 1610 1310, 1145 1130 | 0.6–1.7(14H) 2.9–3.8(5H) 7.5–7.8(1H) 8.0–8.7(4H) 9.4(1H) |
| 9-3 | C$_3$H$_7$ | —CH$_2$CH(CH$_3$)— | 1.43 | 2.0 | 20 | 100 | 12 | (20) | 0.36 g (37%) | 321 | 2930, 1610 1310, 1150 1130 | 0.7–1.6(11H) 2.9–3.8(5H) 7.5–7.8(1H) 8.1–8.8(4H) 9.4(1H) |
| 9-4 | C$_6$H$_{13}$ | —CH(CH$_3$)CH$_2$CH$_2$— | 1.60 | 2.0 | 20 | 80 | 8 | (21) | 0.40 g (35%) | 377 | 2925, 1615 1315, 1145 1125 | 0.7–1.9(20H) 2.9–3.9(5H) 7.5–7.8(1H) 8.1–8.7(4H) 9.3(1H) |
| 9-5 | C$_2$H$_5$ | —(CH$_2$)$_4$CH(CH$_3$)— | 1.26 | 2.0 | 20 | 100 | 15 | (22) | 0.17 g (20%) | 349 | 2920, 1610 1310, 1145 1125 | 0.8–1.9(15H) 3.0–3.6(6H) 7.4–7.7(1H) 8.0–8.6(4H) 9.4(1H) |
| 9-6 | C$_6$H$_{13}$ | —CH$_2$CH$_2$CH(CH$_3$)— | 1.33 | 2.0 | 20 | 100 | 15 | (23) | 0.29 g (31%) | 377 | 2925, 1610 1315, 1145 1125 | 0.6–2.0(19H) 2.5–3.8(6H) 7.6–7.9(1H) 8.0–8.6(4H) 9.4(1H) |
| 9-7 | C$_6$H$_{13}$ | —CH(C$_3$H$_7$)(CH$_2$)$_2$— | 1.40 | 2.0 | 20 | 80 | 6 | (24) | 0.26 g (26%) | 405 | 2920, 1615 1315, 1145 1125 | 0.6–2.1(24H) 2.3–3.7(5H) 7.5–7.8(1H) 8.1–8.7(4H) 9.3(1H) |

To 3.96 g of the thus obtained N-ethyl-N-(2-p-toluenesulfonyloxyethyl)-5-isoquinolinesulfonamide were added 1.25 g of hexylamine, 1.14 g of potassium carbonate and 20 ml of dioxane. The mixture thus obtained was heated in a pressure vessel at 110° C. for 72 following data.

IR absorption spectrum (cm$^{-1}$): 2920, 1610, 1320, 1150, 1130.

NMR spectrum (CDCl₃): 0.6–1.6(14H), 2.2–2.8(4H), 3.1–3.6(4H), 7.4–7.7(1H), 8.0–8.8(4H), 9.3(1H).

Mass spectrum (m/e): 363.

In substantially the same manner as described above except that the reaction conditions were changed as indicated in Table 10-1, N-(2-p-toluenesulfonyloxyethyl)-N-methyl-5-isoquinolinesulfonamide, N-(2-p-toluenesuslfonyloxyethyl)-N-ethyl-5-isoquinolinesulfonamide, N-(2-p-toluenesulfonyloxyethyl)-N-hexyl-5-isoquinolinesulfonamide, N-(2-p-toluenesulfonyloxyethyl)-N-benzyl-5-isoquinolinesulfonaminde, N-butyl-N-(2-p-toluenesulfonyloxyethyl)-5-isoquinolinesulfonamide, N-(3-p-toluenesulfonyloxypropyl)-N-hexyl-5-isoquinolinesulfonamide, N-(6-p-toluenesulfonyloxyhexyl)-N-pentyl-5-isoquinolinesulfonamide, N-(6-p-toluenesulfonyloxyhexyl)-N-hexyl-5-isoquinolinesulfonamide, N-hexyl-N-(2-p-toluenesulfonyloxy-1-methylethyl)5-isoquinolinesulfonamide, N-(4-p-toluenesulfonyloxy-1-methylbutyl)-N-propyl-5-isoquinolinesulfonamide and N-methyl-N-(6-p-toluenesulfonyloxy-5-methylhexyl)-5-isoquinolinesulfonamide, each represented by the formula (XIV), were respectively reacted with the compounds of the formula (XV) as indicated in Table 10-1. There were obtained N-(2-methylaminoethyl)-N-methyl-5-isoquinolinesulfonamide [Compound (25)], N-(2-ethylaminoethyl)-N-ethyl-5-isoquniolinesulfonamide [Compound (26)], N-(2-butylaminoethyl)-N-hexyl-5-isoquinolinesulfonamide [Compound (27)], N-(2-hexylaminoethyl)-N-hexyl-5-isoquinolinesulfonamide [Compound (29)], N-(2-benzylaminoethyl)-N-benzyl-5-isoquinolinesulfonamide [Compound (30)], N-butyl-N-(2-phenylethylaminoethyl)-5-isoquinolinesulfonamide [Compound (31)], N-(2-benzylamioethyl)-N-hexyl-5-isoquinolinesulfonamide [Compound (32)], N-(3-hexylaminopropyl)-N-hexyl-5-isoquinolinesulfonamide [Compound (33)], N-(6-benzylaminohexyl)-N-pentyl-5-isoquinolinesulfonamide [Compound (34)], N-(6-hexylaminohexyl)-N-hexyl-5-isoquinolinesulfonamide [Compound (35)], N-hexyl-N-(2-isopropylamino-1-methylethyl)-5-isoquinolinesulfonamide [Compound (39)], N-(4benzylamino-1-methylbutyl)-N-propyl-5-isoqinolinesulfonamide [Compound (40)] and N-methyl-N-(6-propylamino-5-methylhexyl)-5-isoquinolinesulfonamide [Compound (41)]. The yields and analytical values of these compounds are shown in Table 10-2.

EXAMPLE 20

To 25 ml of an anhydrous methanol solution containing 5.0 g of N-acetonyl-N-hexyl-5-isoquinolinesulfonamide was added 50 ml of an anhydrous methanol solution containing 3.28 g of ethylamine hydrochloride and 344 mg of sodium cyanoborohydride, followed by stirring at 20° C. for 15 hours.

TABLE 10

| Run No. | Compound (XXXI) R² | A | (g) | Compound (XV) | (g) | Reaction medium (ml) | Reaction temperature (°C.) | Reaction time (hr) |
|---|---|---|---|---|---|---|---|---|
| 10-1 | CH₃ | —CH₂— | 1.05 | H₂NCH₃ | 0.15 | EtOH 20 | 80 | 6 |
| 10-2 | C₂H₅ | " | 1.08 | H₂NC₂H₅ | 0.20 | EtOH 20 | 80 | 6 |
| 10-3 | C₆H₁₃ | " | 1.23 | H₂NC₄H₉ | 0.30 | CHCl₃ 20 | 80 | 12 |
| 10-4 | " | " | 1.23 | H₂NC₆H₁₃ | 0.50 | CHCl₃ 20 | 80 | 12 |
| 10-5 | C₇H₇ | " | 1.24 | H₂NCH₂C₆H₅ | 0.50 | dioxane 20 | 110 | 72 |
| 10-6 | C₄H₉ | " | 1.16 | H₂N(CH₂)₂C₆H₅ | 0.50 | dioxane 20 | 110 | 72 |
| 10-7 | C₆H₁₃ | " | 1.23 | H₂NCH₂C₆H₅ | 0.50 | dioxane 20 | 110 | 72 |
| 10-8 | " | —(CH₂)₂— | 1.26 | H₂NC₆H₁₃ | 0.50 | dioxane 20 | 110 | 72 |
| 10-9 | C₅H₁₁ | —(CH₂)₅— | 1.33 | H₂NCH₂C₆H₅ | 0.50 | dioxane 20 | 110 | 72 |
| 10-10 | C₆H₁₃ | " | 1.36 | H₂NC₆H₁₃ | 0.50 | dioxane 20 | 110 | 72 |
| 10-11 | " | —CH— \| CH₃ | 1.26 | H₂NCH(CH₃)₂ | 0.30 | EtOH 20 | 110 | 72 |
| 10-12 | C₃H₇ | —CH(CH₂)₂— \| CH₃ | 1.23 | H₂NCH₂C₆H₅ | 0.50 | dioxane 20 | 80 | 24 |
| 10-13 | CH₃ | —(CH₂)₄CH— \| CH₃ | 1.23 | H₂NC₃H₇ | 0.30 | EtOH 20 | 80 | 24 |

TABLE 10-continued $$\text{(XXXI)} \xrightarrow{\text{HN}R^4R^5 \text{ (XV)}} \text{(XXXIII)}$$

where (XXXI) is the isoquinoline-SO$_2$N(R$^2$)-A-CH$_2$OSO$_2$-C$_6$H$_4$-CH$_3$ and (XXXIII) is the isoquinoline-SO$_2$N(R$^2$)-A-CH$_2$N(R$^4$)R$^5$.

| Run No. | Obtained compound (XXXIII) | Yield | Mass spectrum (m/e) | IR spectrum (cm$^{-1}$) | NMR spectrum (CDCl$_3$) |
|---|---|---|---|---|---|
| 10-1 | (25) | 0.53 g (76%) | 279 | 3330, 2940 1620, 1460 1330, 1165 1145 | 1.8(1H), 2.4(s)(3H) 2.9(s)(3H), 2.5–2.9(2H) 3.0–3.5(2H), 7.5–7.8(1H) 8.0–8.7(4H), 9.3(1H) |
| 10-2 | (26) | 0.57 g (75%) | 307 | 3300, 2930 1620, 1450 1330, 1160 1140 | 0.7–1.5(7H), 2.4(t)(2H) 2.7(t)(2H), 3.2–3.6(4H) 7.5–7.8(1H), 8.0–8.7(4H) 9.4(1H) |
| 10-3 | (27) | 0.68 g (70%) | 391 | 2930, 1620 1440, 1310 1160, 1140 | 0.6–1.8(19H), 2.2–2.9(4H) 3.0–3.7(4H), 7.5–7.8(1H) 8.5–8.8(4H), 9.4(1H) |
| 10-4 | (29) | 0.68 g (65%) | 419 | 2930, 1620 1450, 1310 1150, 1130 | 0.6–1.7(23H), 2.2–2.9(4H) 3.0–3.6(4H), 7.5–7.8(1H) 8.5–8.8(4H), 9.3(1H) |
| 10-5 | (30) | 0.75 g (70%) | 431 | 3380, 1615 1450, 1325 1145, 1130 | 2.8–3.1(2H), 3.5–4.0(2H) 4.1(2H), 4.6(2H), 7.3(5H) 7.4(2H), 7.7–8.0(1H) 8.3–8.8(4H), 9.4(1H) |
| 10-6 | (31) | 0.70 g (68%) | 411 | 3350, 1620 1450, 1320 1160, 1140 | 0.6–1.8(8H), 2.7–3.2(4H) 3.5–4.0(6H), 7.2(5H) 7.7–8.0(1H), 8.3–8.8(4H) 9.5(1H) |
| 10-7 | (32) | 0.69 g (65%) | 425 | 2920, 1610 1440, 1310 1160, 1140 | 0.6–1.7(12H), 2.7(t)(2H) 3.0–3.6(4H), 3.62(s)(2H) 7.1(s)(5H), 7.4–7.8(1H) 8.0–8.7(4H), 9.3(1H) |
| 10-8 | (33) | 0.43 g (40%) | 433 | 2930, 1615 1450, 1320 1150, 1130 | 0.6–2.0(25H), 2.2–2.9(4H) 3.0–3.6(4H), 7.5–7.8(1H) 8.5–8.8(4H), 9.3(1H) |
| 10-9 | (34) | 0.58 g (50%) | 467 | 2920, 1620 1440, 1330 1160, 1140 | 0.6–1.9(18H), 2.5–3.9(6H) 4.0(2H), 7.3(5H) 7.4–7.8(1H), 8.0–8.7(4H) 9.4(1H) |
| 10-10 | (35) | 0.42 g (35%) | 475 | 2900, 1630 1450, 1335 1170, 1150 | 0.7–2.0(31H), 2.0–3.8(8H) 7.5–7.9(1H), 8.1–8.7(4H) 9.3(1H) |
| 10-11 | (36) | 0.59 g (60%) | 391 | 2930, 1620 1450, 1350 1160, 1140 | 0.6–1.8(21H), 2.2–2.7(3H) 3.3–3.6(3H), 7.4–7.7(1H) 8.0–8.8(4H), 9.3(1H) |
| 10-12 | (37) | 0.67 g (63%) | 425 | 2920, 1620 1440, 1320 1160, 1140 | 0.7–1.8(13H), 2.2–2.6(2H) 2.7–3.9(3H), 4.1(2H) 7.2(5H), 7.4–7.7(1H) 8.0–8.7(4H), 9.4(1H) |
| 10-13 | (38) | 0.50 g (53%) | 377 | 2925, 1620 1440, 1330 1170, 1150 | 0.7–1.8(16H), 2.3–3.2(4H) 3.2–3.7(5H), 7.6–7.9(1H) 8.0–8.7(4H), 9.3(1H) |

To the mixture obtained was added 1.67 g of potassium hydroxide, and the resultant mixture was stirred for 16 minutes, followed by extraction twice with 50 ml of chloroform. The chloroform layer was dried with anydrous sodium sulfate, and the solvent was removed under reduced pressure to obtain a residue. The residue thus obtained was subjected to purification by silica gel column chromatography (Wacogel C-200, 100 g; solvent: chloroform) to obtain 2.76 g of N-(2-ethylaminopropyl)-N-hexyl-5-isoquinolinesulfonamide [Coompound (36)]. Compound (36) was analyzed to give the following data.

IR absorption spectrum (cm$^{-1}$): 2925, 1615, 1450, 1320, 1150, 1130.

NMR spectrum (CDCl$_3$): 0.6–1.7(17H), 2.2—3.7(7H), 7.4–7.7(1H), 8.0–8.8(4H), 9.3(1H).

Mass spectrum (m/e): 377.

In substantially the same manner as described above except that the reaction conditions were changed as indicated in Table 11-1, N-(2-hexylaminopropyl)-N-hexyl-5-isoquinolinesulfonamide [Compound (37)] was prepared from N-acetonyl-N-hexyl-5-isoquinolinesulfonamide, and N-(2-propylaminooctyl)-N-butyl-5-isoquinolinesulfonamide [Compound (38)] was prepared from N-butyl-N-(2-oxooctyl)-5-isoquinolinesulfonamide. The yields and analytical values of these compounds are shown in Table 11-2.

EXAMPLE 21

In 30 ml of ethanol were dissolved 5.47 g of N-hexyl-N-(2-p-toluenesulfonyloxyethyl)-5-isoquinolinesulfonamide and 2.85 g of piperidine, and the solution was heated in a pressure vessel at 80° C. for 3 hours. To the mixture obtained was added 100 ml of chloroform, and the resultant mixture was washed with 100 ml of water and dried with anhydrous magnesium sulfate. The chloroform was removed under reduced pressure to obtain a residue. The residue thus obtained was subjected to purification by silica gel column chromatography (Wacogel C-200, solvent: 3% methanol solution in chloroform) to obtain 3.6 g of N-hexyl-N-(2-piperidinoethyl)-5-isoquinolinesulfonamide [Compound (45)]. Compound (45) was analyzed to give the following data.

IR absorption spectrum (cm$^{-1}$): 293,01620,1330,1160,1130.

NMR spectrum (CDCl$_3$): 0.6–1.6(17H), 1.8–2.8(6H), 3.1–3.6(4H), 7.5–7.8(1H), 8.2–8.9(4H), 9.3(1H).

Mass spectrum (m/e): 403.

tained N-(2-diethylaminoethyl)-N-methyl-5-isoquinolinesulfonamide [Compound (42)], N-(2-dimethylaminoethyl)-N-hexyl-5-isoquinolinesulfonamide [Compound (43)], N-benzyl-N-(2-dihexylamimoethyl)-5-isoquinolinesulfonamide [Compound (44)], N-hexyl-N-(2-morpholinoethyl)-5-isoquinolinesulfonamide [Compound (46)], N-[3-(N-cyclohexyl-N-methylamino)ethyl]-N-ethyl-5-isoquinolinesulfonamide [Compound (47)], N-hexyl-N-(2-piperidinopropyl)-5-isoquinolinesulfonamide [Compound (48), N-(2-diethylamino-1-methylethyl)-N-hexyl-5-isoquinolinesulfonamide [Compound (49)] and N-ethyl-N-( 5-piperidinopentyl)-5-isoquinolinesulfonamide [Compound (50)]. The yields and analytical values of these compounds are shown in Table 12-2.

EXAMPLE 22

TABLE 11

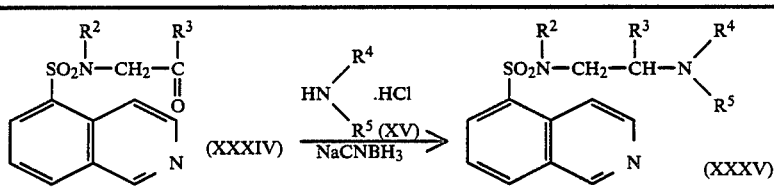

| Run No. | Compound (XXXIV) R$^2$ | R$^3$ | Compound (XV).HCl (g) | NaCNBH$_3$ (g) | Reaction temperature (°C.) | Reaction time (hr) | Obtained compound (XXXV) | Yield | Mass spectrum (m/e) | IR spectrum (cm$^{-1}$) | NMR spectrum (CDCl$_3$) |
|---|---|---|---|---|---|---|---|---|---|---|---|
| 11-1 | C$_6$H$_{13}$ | CH$_3$ | 1.4 H$_2$NC$_6$H$_{13}$ 0.69 | 0.25 | 20–25 | 18 | (37) | 0.61 g (35%) | 433 | 2930, 1620 1330, 1160 1140 | 0.7–1.7(25H) 1.9–3.1(3H) 3.1–3.7(4H) 7.7–8.0(1H) 8.3–9.0(4H) 9.1(1H) |
| 11-2 | C$_4$H$_9$ | C$_6$H$_{13}$ | 1.6 H$_2$NC$_3$H$_7$ 0.48 | 0.25 | 20–25 | 15 | (38) | 0.52 g (30%) | 433 | 2920, 1620 1340, 1160 1140 | 0.6–1.8(26H) 2.5–3.6(7H) 7.6–8.0(1H) 8.1–8.9(4H) 9.3(1H) |

In substantially the same manner as described above except that the reaction conditions were changed as indicated in Table 12-1, N-methyl-N-(2-p-toluenesulfonyloxyethyl)-5-isoquinolinesulfonamide, N-hexyl-N-(2-p-toluenesulfonyloxyethyl)-5-isoquinolinesulfonamide, N-benzyl-N-(2-p-toluenesulfonyloxyethyl)-5-isoquinolinesulfonamide, N-ethyl-N-(2-p-toluenesulfonyloxyethyl)-5-isoquinolinesulfonamide, N-hexyl-N-(2-p-toluenesulfonyloxypropyl)-5-isoquinolinesulfonamide, N-hexyl-N-(2-p-toluenesulfonyloxy-1-methylethyl)-5-isoquinolinesulfonamide and N-ethyl-N-(5-p-toluenesulfonyloxypentyl)-5-isoquinolinesulfonamide were respectively reacted with the compounds of formula (XV) as indicated in Table 12-1. There were ob- To 10 g of 1-(1-chloro-5-isoquinolinesulfonyl)-3aminopiperidine was added 100 ml of a 6 mol/1 aqueous hydrochloric acid solution, and the mixture was heated at 65° C. for 6 hours, whereby crystals separated out. The crystals were filtered off, washed twice with 30 ml of ice water and further twice with 30 ml of ethanol, and dried to obtain 9.08 g of 1-(1-hydroxy-5-isoquinolinesulfonyl)-3-aminopiperidine [Compound (84)]. Compound (84) was analyzed to give the following data.

IR absorption spectrum (cm$^{-1}$): 1680,1625,1305,1160.

NMR spectrum (CDCl$_3$-DCl): 0.6–2.0(4H), 2.1–3.2(3H), 3.3–3.8(2H), 7.4–7.9(1H), 8.0–8.7(4H).

TABLE 12

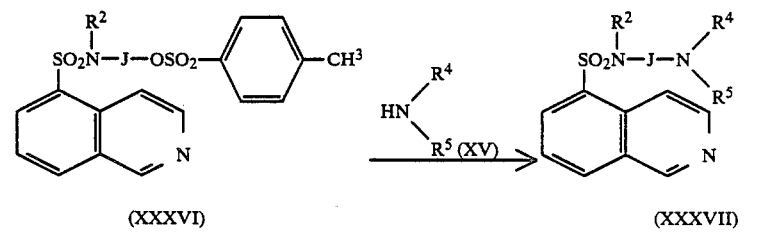

| Run | Compound (XXXVI) | Compound (XV) | Reaction medium | Reaction temperature | Reaction time |
|---|---|---|---|---|---|

TABLE 12-continued

| No. | R² | J | (g) | (g) | | (ml) | (°C.) | (hr) |
|---|---|---|---|---|---|---|---|---|
| 12-1 | CH₃ | —(CH₂)₂— | 1.68 | HNEt₂ 0.44 | | EtOH 10 | 100 | 6 |
| 12-2 | C₆H₁₃ | " | 1.96 | HNMe₂ 0.27 | | EtOH 10 | 100 | 6 |
| 12-3 | CH₂C₆H₅ | " | 1.98 | HN(C₆H₁₃)₂ 1.11 | | dioxane 10 | 110 | 24 |
| 12-4 | C₆H₁₃ | " | 1.96 | 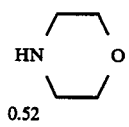 0.52 | HN○O | dioxane 10 | 110 | 24 |
| 12-5 | C₂H₅ | " | 1.30 | 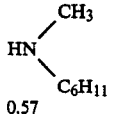 0.57 | HN(CH₃)(C₆H₁₁) | CHCl₃ 10 | 90 | 24 |
| 12-6 | C₆H₁₃ | —CH₂CH— \| CH₃ | 1.51 | 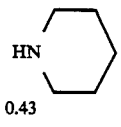 0.43 | HN○ | dioxane 10 | 110 | 6 |
| 12-7 | C₆H₁₃ | —CHCH₂— \| CH₃ | 1.51 | HNEt₂ 0.37 | | EtOH 10 | 90 | 6 |
| 12-8 | C₂H₅ | —(CH₂)₅— | 1.43 | 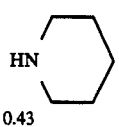 0.43 | HN○ | dioxane 10 | 90 | 8 |

| Run No. | Obtained compound (XXXVII) | Yield | Mass spectrum (m/e) | IR spectrum (cm⁻¹) | NMR spectrum (CDCl₃) |
|---|---|---|---|---|---|
| 12-1 | (42) | 1.04 g (81%) | 321 | 2960, 1625, 1310, 1170, 1150 | 1.93(t)(6H), 2.0–2.9(11H), 7.5–7.8(1H), 8.2–8.9(4H), 9.4(1H) |
| 12-2 | (43) | 0.99 g (68%) | 363 | 2950, 1620, 1310, 1170, 1150 | 0.6–1.8(11H), 2.0–3.0(12H), 7.4–7.7(1H), 8.2–8.8(4H), 9.3(1H) |
| 12-3 | (44) | 1.18 g (58%) | 509 | 2940, 1625, 1315, 1170, 1150 | 0.6–2.0(22H), 2.5–3.1(4H), 4.2(2H), 7.3(5H), 7.5–7.8(1H), 8.2–8.8(4H), 9.4(1H) |
| 12-4 | (46) | 1.25 g (77%) | 405 | 2940, 1625, 1315, 1170, 1150 | 0.5–1.7(11H), 2.7–3.8(14H), 7.4–7.7(1H), 8.2–8.7(4H), 9.3(1H) |
| 12-5 | (47) | 0.68 g (60%) | 375 | 2925, 1620, 1315, 1170, 1150 | 0.6–2.0(13H), 2.6–3.7(10H), 7.5–7.8(1H), 8.2–8.8(4H), 9.4(1H) |
| 12-6 | (48) | 0.94 g (75%) | 417 | 2925, 1620, 1330, 1130, 1140 | 0.8–2.4(24H), 2.7–3.5(5H), 7.5–7.8(1H), 8.2–8.9(4H), 9.3(1H) |
| 12-7 | (49) | 0.87 g (72%) | 405 | 2925, 1620, 1320, 1170, 1150 | 0.6–1.8(20H), 2.7–3.6(9H), 7.4–7.7(1H), 8.2–8.8(4H), 9.4(1H) |
| 12-8 | (50) | 0.79 g (68%) | 389 | 2940, 1625, 1315, 1170, 1150 | 0.5–1.6(15H), 2.7–3.5(10H), 7.4–7.7(1H), 8.2–8.7(4H), 9.3(1H) |

In substantially the same manner as described above except that the reaction conditions were changed as indicated in Table 13-1, there were obtained 1-(1-hydroxy-5-isoquinolinesulfonyl)-4-aminopiperidine [Compound (79)], 1-(1-hydroxy-5-isoquinolinesulfonyl)-4-methylaminopiperidine [Compound (80)], 1-(1-hydroxy-5-isoquinolinesulfonyl)-4-propylaminopiperidine [Compound (81)], 1-(1-hydroxy-5-isoquinolinesulfonyl)-4-phenylaminopiperidine [Compound (82)], 1-(1-hydroxy-5-isoquinolinesulfonyl)-4-benzylaminopiperidine Compound (83)], 1-(1-hydroxy-5-isoquinolinesulfonyl)-3-propylaminopiperidine [Compound (85)], 1-(1-hydroxy-5-isoquinolinesulfonyl)-3-benzylaminopiperidine [Compound (86)], 1-(1-hydroxy-5-isoquinolinesulfonyl)-3-phenylaminopiperidine [Compound (87)], 1-(1-hydroxy-5-isoquinolinesulfonyl)-3-hexylaminopiperidine [Compound (88)], 1-(1-hydroxy-5-isoquinolinesulfonyl)-3-phenethylaminopiperidine [Compound (89)] and 1-(1-hydroxy-5-isoquinolinesulfonyl)-3-dimethylaminopiperidine [Compound (90)]. The yields and analytical values of these compounds are shown in Table 13-2.

EXAMPLE 23

In 20 ml of methanol was dissolved 1.0 g of 1-(5-isoquinolinesulfonyl)-3-aminopiperidine. To the solution was added 1N hydrochloric acid so that the pH of the solution became 6.0. Then, the solvent was removed under reduced pressure to obtain a residue. The residue thus obtained was subjected to recrystallization using methanol to obtain 0.81 g of 1-(5-isoquinolinesulfonyl)-3-aminopiperidine hydrochloride.

TABLE 13

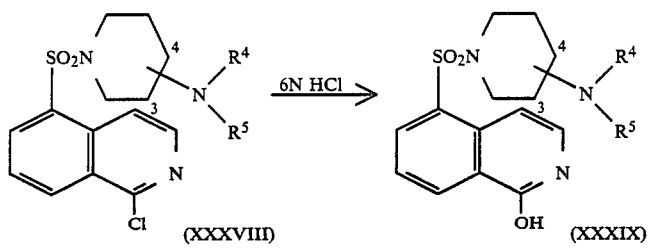

| Run No. | Compound (XXXVIII) −N(R⁴)(R⁵) | (g) | 6N HCl (ml) | Reaction temperature (°C.) | Reaction time (hr) | Obtained compound (XXXIX) | Yield | IR spectrum (cm⁻¹) | NMR spectrum (CD₃OD—DCl) |
|---|---|---|---|---|---|---|---|---|---|
| 13-1 | —NH₂ (4-position) | 2.0 | 15 | 60 | 4 | (79) | 1.62 g (81%) | 1680, 1625, 1305, 1160 | 1.3–1.7(4H), 2.9–3.3(5H) 7.4–7.9(1H), 8.0–8.7(4H) |
| 13-2 | —NHCH₃ (4-position) | 2.0 | 15 | 60 | 4 | (80) | 1.60 g (81%) | 1680, 1625, 1305, 1160 | 1.3–2.2(4H), 2.3–3.5(8H) 7.4–7.9(1H), 8.0–8.7(4H) |
| 13-3 | —NHC₃H₇ (4-position) | 2.0 | 15 | 60 | 6 | (81) | 1.60 g (84%) | 1680, 1625, 1305, 1160 | 0.8–2.2(9H), 2.3–3.1(5H) 3.2–4.1(2H), 7.4–7.9(1H) 8.0–8.7(4H) |
| 13-4 | —NHC₆H₅ (4-position) | 3.0 | 20 | 60 | 6 | (82) | 2.0 g (70%) | 1680, 1625, 1305, 1160 | 0.8–2.1(4H), 2.3–3.1(3H) 3.7–4.1(2H), 7.4–7.9(6H) 8.0–8.7(4H) |
| 13-5 | —NHCH₂C₆H₅ (4-position) | 3.0 | 20 | 80 | 6 | (83) | 2.12 g (74%) | 1680, 1625, 1305, 1160 | 0.8–3.2(7H), 3.7–4.1(4H) 7.4–7.9(6H), 8.0–8.7(4H) |
| 13-6 | —NHC₃H₇ (3-position) | 2.0 | 15 | 80 | 3 | (85) | 1.49 g (79%) | 1680, 1625, 1305, 1160 | 0.8–2.1(9H), 2.3–3.1(5H) 3.7–4.1(2H), 7.4–7.9(1H) 8.0–8.7(4H) |
| 13-7 | —NHCH₂C₆H₅ (3-position) | 3.0 | 20 | 80 | 3 | (86) | 2.29 g (80%) | 1680, 1625, 1305, 1160 | 0.8–2.0(4H), 2.1–3.2(3H) 3.3–4.0(4H), 7.4–7.9(1H) 8.0–8.7(4H) |
| 13-8 | —NHC₆H₅ (3-position) | 3.0 | 20 | 80 | 3 | (87) | 2.17 g (76%) | 1680, 1625, 1305, 1160 | 0.8–2.0(4H), 2.1–3.2(3H) 3.3–4.0(4H), 7.4–7.9(6H) 8.0–8.7(4H) |
| 13-9 | —NHC₆H₁₃ (3-position) | 2.0 | 15 | 80 | 3 | (88) | 1.57 g (82%) | 1680, 1625, 1305, 1160 | 0.8–2.0(15H), 2.1–3.2(5H) 3.3–4.0(2H), 7.4–7.9(1H) 8.0–8.7(4H) |
| 13-10 | —NH(CH₂)₂C₆H₅ (3-position) | 1.70 | 15 | 60 | 4 | (89) | 0.99 g (61%) | 1680, 1625, 1305, 1160 | 0.8–2.2(6H), 2.2–3.2(4H) 3.3–4.1(3H), 7.4–7.9(1H) 8.0–8.7(4H) |
| 13-11 | —NMe₂ (3-position) | 2.0 | 15 | 60 | 4 | (90) | 1.42 g (75%) | 1680, 1625, 1305, 1160 | 0.8–2.2(4H), 2.3–3.2(9H) 3.3–4.0(2H), 7.4–7.9(1H) 8.0–8.7(4H) |

This compound was analyzed to give the following data.

Elementary analysis (%): Found value: C,51.45; H,5.71; N,12.99. Calculated value: C,51.29; H,5.53; N,12.82.

EXAMPLE 24

To 1.34 g of N-(2-aminoethyl)-N-hexyl-5-isoquinolinesulfonamide [Compound (4)] was added 100 ml of water. Then, the pH of the solution was adjusted to 5 with hydrochloric acid. The mixture was lyophilized to obtain a residue. The residue thus obtained was subjected to recrystallization using a mixture consisting of 5% by weight of ethanol and 95% by weight of acetone to obtain 0.7 g of N-(2-aminoethyl)-N-hexy-5-isoquinolinesulfonamide hydrochloride. This compound was analyzed to give the following data.

Elementary analysis (%): Found value: C,54.70; H,6.95; N,11.10. Calculated value: C,54.90; H,7.05; N,11.30.

APPLICATION EXAMPLE 1

The effect of the compounds of the present invention on relaxation of mesenteric artery was examined according to the method as mentioned hereinbefore. The obtained $ED_{50}$ values are shown in Table 14.

APPLICATION EXAMPLE 2

The effects (dilation of the arteries) of the compounds of the present invention on blood flow in coronary, vertebral and femoral arteries were examined according to the method as mentioned hereinbefore. The results are shown in Table 15.

APPLICATION EXAMPLE 3

The effect of the compounds of the present invention on relaxation of bronchial tubes was examined according to the method as mentioned hereinbefore. The obtained $ED_{50}$ values are shown in Table 16.

APPLICATION EXAMPLE 4

Compounds of the present invention were tested with respect to acute toxicities according to the method as mentioned hereinbefore. The results are shown in Table 17.

TABLE 14

| Compound No. | ED$_{50}$ (µM) | Compound No. | ED$_{50}$ (µM) |
|---|---|---|---|
| (1) | 5 | (51) | 15 |
| (2) | 4 | (52) | 14 |
| (3) | 2 | (53) | 14 |
| (4) | 1 | (54) | 13 |
| (5) | 2 | (55) | 17 |
| (6) | 4 | (56) | 14 |
| (7) | 2 | (57) | 15 |
| (8) | 5 | (58) | 20 |
| (9) | 9 | (59) | 21 |
| (10) | 15 | (60) | 19 |
| (11) | 3 | (61) | 15 |
| (12) | 4 | (62) | 22 |
| (13) | 5 | (63) | 3 |
| (14) | 10 | (64) | 6 |
| (15) | 7 | (65) | 6 |
| (16) | 13 | (66) | 5 |
| (17) | 14 | (67) | 14 |
| (18) | 13 | (68) | 16 |
| (19) | 16 | (69) | 8 |
| (20) | 17 | (70) | 7 |
| (21) | 19 | (71) | 4 |
| (22) | 21 | (72) | 24 |
| (23) | 18 | (73) | 19 |
| (24) | 23 | (75) | 20 |
| (25) | 10 | (76) | 13 |
| (26) | 11 | (77) | 16 |
| (27) | 13 | (78) | 12 |
| (28) | 10 | (79) | 15 |
| (29) | 9 | (80) | 14 |
| (30) | 12 | (81) | 12 |
| (31) | 10 | (82) | 21 |
| (32) | 8 | (83) | 18 |
| (33) | 13 | (84) | 13 |
| (34) | 20 | (85) | 13 |
| (35) | 19 | (86) | 17 |
| (36) | 7 | (87) | 20 |
| (37) | 6 | (88) | 12 |
| (38) | 8 | (89) | 12 |
| (39) | 11 | (90) | 23 |
| (40) | 14 | (94) | 18 |
| (41) | 17 | (95) | 14 |
| (42) | 15 | (96) | 15 |
| (43) | 20 | (97) | 15 |
| (44) | 21 | (98) | 13 |
| (45) | 23 | (99) | 21 |
| (46) | 23 | (100) | 22 |
| (47) | 22 | (101) | 17 |
| (48) | 24 | (102) | 16 |
| (50) | 26 | | |

TABLE 15

| Compound No. | Dose (mg/kg) | Increase in coronary artery blood flow (%) | Increase in vertebral artery blood flow (%) | Increase in femoral artery blood flow (%) |
|---|---|---|---|---|
| (3) | 0.3 | 134 | 130 | 25 |
| (4) | 0.3 | 188 | 170 | 38 |
| (28) | 0.3 | 114 | 110 | 31 |
| (63) | 0.3 | 91 | 72 | 20 |
|  | 1.0 | 128 | 95 | 38 |
| (71) | 1.0 | 102 | 85 | 35 |
| (84) | 1.0 | 74 | 51 | 27 |
| Comparative Compound No. 1 | 0.3 | 89 | 160 | 48 |
| Comparative Compound No. 2 | 0.3 | 27 | 48 | 30 |
| Comparative Compound No. 3 | 1.0 | 70 | 98 | 69 |

Comparative Compound No. 1: 1-(5-Isoquinolinesulfonyl)homopiperazine
Comparative Compound No. 2: 1-(1-Hydroxy-5-isoquinolinesulfonyl)-homopiperazine
Comparative Compound No. 3: 1-(5-Isoquinolinesulfonyl)piperazine

TABLE 16

| Compound No. | ED$_{50}$ (µM) | Compound No. | ED$_{50}$ (µm) |
|---|---|---|---|
| (1) | 8 | (50) | 26 |
| (2) | 5 | (51) | 8 |
| (3) | 5 | (52) | 12 |
| (4) | 3 | (53) | 11 |
| (5) | 6 | (54) | 14 |
| (6) | 5 | (55) | 12 |
| (7) | 13 | (56) | 10 |
| (8) | 11 | (57) | 20 |
| (9) | 15 | (58) | 25 |
| (10) | 16 | (59) | 23 |
| (11) | 9 | (60) | 13 |
| (12) | 12 | (61) | 15 |
| (13) | 19 | (62) | 23 |
| (14) | 22 | (63) | 3 |
| (15) | 25 | (64) | 6 |
| (16) | 13 | (65) | 5 |
| (17) | 10 | (66) | 8 |
| (18) | 13 | (67) | 10 |
| (19) | 13 | (69) | 14 |
| (20) | 15 | (70) | 13 |
| (21) | 17 | (71) | 10 |
| (22) | 20 | (72) | 21 |
| (23) | 18 | (73) | 26 |
| (24) | 17 | (75) | 16 |
| (25) | 10 | (76) | 27 |
| (26) | 8 | (77) | 32 |
| (27) | 13 | (78) | 30 |
| (28) | 9 | (79) | 13 |
| (29) | 10 | (80) | 16 |
| (30) | 12 | (81) | 14 |
| (31) | 15 | (82) | 21 |
| (32) | 17 | (83) | 19 |
| (33) | 19 | (84) | 8 |
| (34) | 21 | (85) | 11 |
| (35) | 25 | (86) | 11 |
| (36) | 30 | (87) | 15 |
| (37) | 27 | (88) | 9 |
| (38) | 23 | (89) | 10 |
| (39) | 20 | (90) | 17 |
| (40) | 22 | (94) | 22 |
| (41) | 22 | (95) | 18 |
| (42) | 25 | (96) | 12 |
| (43) | 27 | (97) | 10 |
| (44) | 29 | (98) | 13 |
| (45) | 17 | (99) | 19 |
| (46) | 25 | (100) | 22 |
| (47) | 19 | (101) | 14 |
| (48) | 20 | (102) | 18 |
| (49) | 15 | | |

TABLE 17

| Compound No. | LD$_{50}$ (mg/kg) male mice i.v.[1] | male mice p.o.[2] | male rat i.v.[1] | male rat p.o.[2] |
|---|---|---|---|---|
| (3) | 105 | — | — | — |
| (4) | 95 | 1100 | 131 | 968 |
| (28) | 145 | — | — | — |
| (63) | 176 | 1122 | 194 | 1215 |

TABLE 17-continued

| | LD$_{50}$ (mg/kg) | | | |
| --- | --- | --- | --- | --- |
| | male mice | | male rat | |
| Compound No. | i.v.[1] | p.o.[2] | i.v.[1] | p.o.[2] |
| (84) | 141 | — | — | — |

Note
[1] intravenous administration
[2] administration per os.

What is claimed is:

1. An isoquinoline derivative represented by the formula (I)

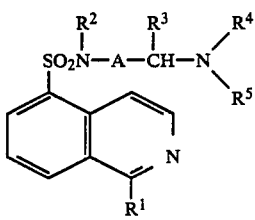

wherein
R$^1$ is selected from the group consisting of a hydrogen atom, a chlorine atom and a hydroxyl group;
R$^2$ is selected from the group consisting of an alkyl group having 1 to 8 carbon atoms and a benzyl group, or directly bonded with R$^3$ to form Z;
R$^3$ is selected from the group consisting of a hydrogen atom and an alkyl group having 1 to 8 carbon atoms, or directly bonded with R$^2$ to form Z;
said Z being selected from the group consisting of an unsubstituted ethylene group, an ethylene group substituted with an alkyl group having 1 to 8 carbon atoms, an unsubstituted trimethylene group, and a trimethylene group substituted with an alkyl group having 1 to 8 carbon atoms;
provided that where R$^2$ and R$^3$ are not directly bonded with each other, R$^1$ is a hydrogen atom, and
where R$^2$ and R$^3$ are directly bonded with each other to form Z, R$^1$ is selected from the group consisting of a hydrogen atom, a chlorine atom and a hydroxyl group;
R$^4$ and R$^5$ are independently selected from the group consisting of a hydrogen atom, an alkyl group having 1 to 6 carbon atoms which is unsubstituted or substituted with a phenyl group, and a phenyl group, or R$^4$ and R$^5$ are each alkylene groups having 1 to 5 carbon atoms and bonded with each other directly or through an oxygen atom to form a heterocyclic ring in cooperation with the adjacent nitrogen atom, the total number of carbon atoms in the two alkylene groups not exceeding 6; and
A is an alkylene group having 1 to 5 carbon atoms which is unsubstituted or substituted with an alkyl group having 1 to 8 carbon atoms;
or a pharmacologically acceptable acid salt thereof.

2. The isoquinoline derivative according to claim 1, wherein R$^1$ is a hydrogen atom; R$^2$ is selected from the group consisting of an alkyl group having 1 to 8 carbon atoms and a benzyl group; R$^3$ is selected from the group consisting of a hydrogen atom and an alkyl group having 1 to 8 carbon atoms; and A is an alkylene group having 1 to 5 carbon atoms which is unsubstituted or substituted with an alkyl group having 1 to 4 carbon atoms.

3. The isoquinoline derivative according to claim 2, wherein R$^3$, R$^4$ and R$^5$ are each hydrogen atoms; and A is an alkylene group having 1 to 5 carbon atoms.

4. The isoquinoline derivative according to claim 3, wherein A is a methylene group.

5. The isoquinoline derivative according to claim 4, wherein R$^2$ is a hexyl group.

6. The isoquinoline derivative according to claim 1, wherein R$^1$ is a hydrogen atom; R$^2$ and R$^3$ are directly bonded with each other to form Z which is selected from the group consisting of an ethylene group which is unsubstituted or substituted with a methyl group and a trimethylene group which is unsubstituted or substituted with a methyl group; and A is selected from the group consisting of a methylene group which is unsubstituted or substituted with a methyl group and an ethylene group which is unsubstituted or substituted with a methyl group.

7. The isoquinoline derivative according to claim 6, wherein R$^2$ and R$^3$ are directly bonded with each other to form a trimethylene group; R$^4$ is a hydrogen atom; R$^5$ is selected from the group consisting of a hydrogen atom, an alkyl group having 1 to 6 carbon atoms which is unsubstituted or substituted with a phenyl group, and a phenyl group; and A is a methylene group.

8. The isoquinoline derivative according to claim 7, wherein R$^5$ is a hydrogen atom.

9. The isoquinoline derivative according to claim 7, wherein R$^5$ is selected from the group consisting of a methyl group, an ethyl group, a propyl group, a butyl group, a hexyl group, a phenyl group, a benzyl group and a phenylethyl group.

10. The isoquinoline derivative according to claim 6, wherein R$^2$ and R$^3$ are directly bonded with each other to form an ethylene group; R$^4$ is a hydrogen atom; R$^5$ is selected from the group consisting of a hydrogen atom, a methyl group, an ethyl group, a propyl group, a butyl group, a hexyl group, a phenyl group, a benzyl group and a phenylethyl group; and A is selected from the group consisting of a methylene group and an ethylene group.

11. The isoquinoline derivative according to claim 1, wherein R$^1$ is selected from the group consisting of a chlorine atom and a hydroxyl group; R$^2$ and R$^3$ are directly bonded with each other to form Z which is selected from the group consisting of an ethylene group which is unsubstituted or substituted with a methyl group and a trimethylene group which is unsubstituted or substituted with a methyl group; and A is selected from the group consisting of a methylene group which is unsubstituted or substituted with a methyl group and an ethylene group which is unsubstituted or substituted with a methyl group.

12. The isoquinoline derivative according to claim 11, wherein R$^2$ and R$^3$ are directly bonded with each other to form a trimethylene group; R$^4$ is a hydrogen atom; R$^5$ is selected from the group consisting of a hydrogen atom, a methyl group, an ethyl group, a propyl group, a butyl group, a hexyl group, a phenyl group, a benzyl group and a phenylethyl group; and A is a methylene group.

13. The isoquinoline derivative according to claim 12, wherein R$^1$ is a hydroxyl group; and R$^5$ is a hydrogen atom.

* * * * *